(12) United States Patent
Holakovsky et al.

(10) Patent No.: US 9,827,384 B2
(45) Date of Patent: Nov. 28, 2017

(54) NEBULIZER

(75) Inventors: Holger Holakovsky, Witten (DE); Ralf Thoemmes, Willich (DE); Marc Rohrschneider, Hagen (DE); Florian Witte, Schwabenheim (DE); Kevin Peter Deane, Fen Ditton (GB); Douglas Ivan Jennings, Royston (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 880 days.

(21) Appl. No.: 13/476,220

(22) Filed: May 21, 2012

(65) Prior Publication Data
US 2013/0125881 A1 May 23, 2013

(30) Foreign Application Priority Data

May 23, 2011 (EP) .................................. 11004236

(51) Int. Cl.
*A61M 15/00* (2006.01)
*A61M 11/02* (2006.01)
(Continued)

(52) U.S. Cl.
CPC ...... *A61M 15/0065* (2013.01); *A61M 11/007* (2014.02); *A61M 11/02* (2013.01); *A61M 15/0025* (2014.02); *A61M 15/0036* (2014.02); *A61M 15/0071* (2014.02); *A61M 15/0081* (2014.02); *A61M 15/0086* (2013.01);
(Continued)

(58) Field of Classification Search
CPC ........ A61M 15/0081; A61M 2205/276; A61M 15/0065; A61M 15/0071; A61M 15/0036; A61M 15/0025; A61M 11/007; A61M 15/0086; A61M 11/02; A61M 11/00; A61M 11/006; A61M 15/00; A61M 15/0068; A61M 15/007; A61M 15/0073; G06M 1/026; G06M 1/24; B05B 11/308; B05B 11/0054; B05B 11/3091; B05B 11/039; B05B 11/0391; F04C 2270/0421
USPC ........... 128/200.14, 200.16, 200.18, 200.19, 128/200.21; 604/141, 143, 151–155
See application file for complete search history.

(56) References Cited

U.S. PATENT DOCUMENTS 1,828,864 A 10/1931 Hopkins
2,015,970 A 10/1935 Schoene
(Continued)

FOREIGN PATENT DOCUMENTS

AU 2005201364 A1 7/2006
CA 1094549 A 1/1981
(Continued)

OTHER PUBLICATIONS

International Search Report and Written Opinion for PCT/EP20112/059463 dated Oct. 25, 2012.
(Continued)

Primary Examiner — Kathryn E Ditmer
(74) Attorney, Agent, or Firm — Marc Began; Philip I. Datlow

(57) ABSTRACT

A nebulizer is proposed which comprises a replaceable container containing fluid, a housing part detachable from the nebulizer for replacing the container, and an operation counter inseparable from the housing part as depicted in exemplary FIG. 10. The operation counter comprises a lead screw and an associated rider both supported by the housing part.

13 Claims, 13 Drawing Sheets

Figure 1:
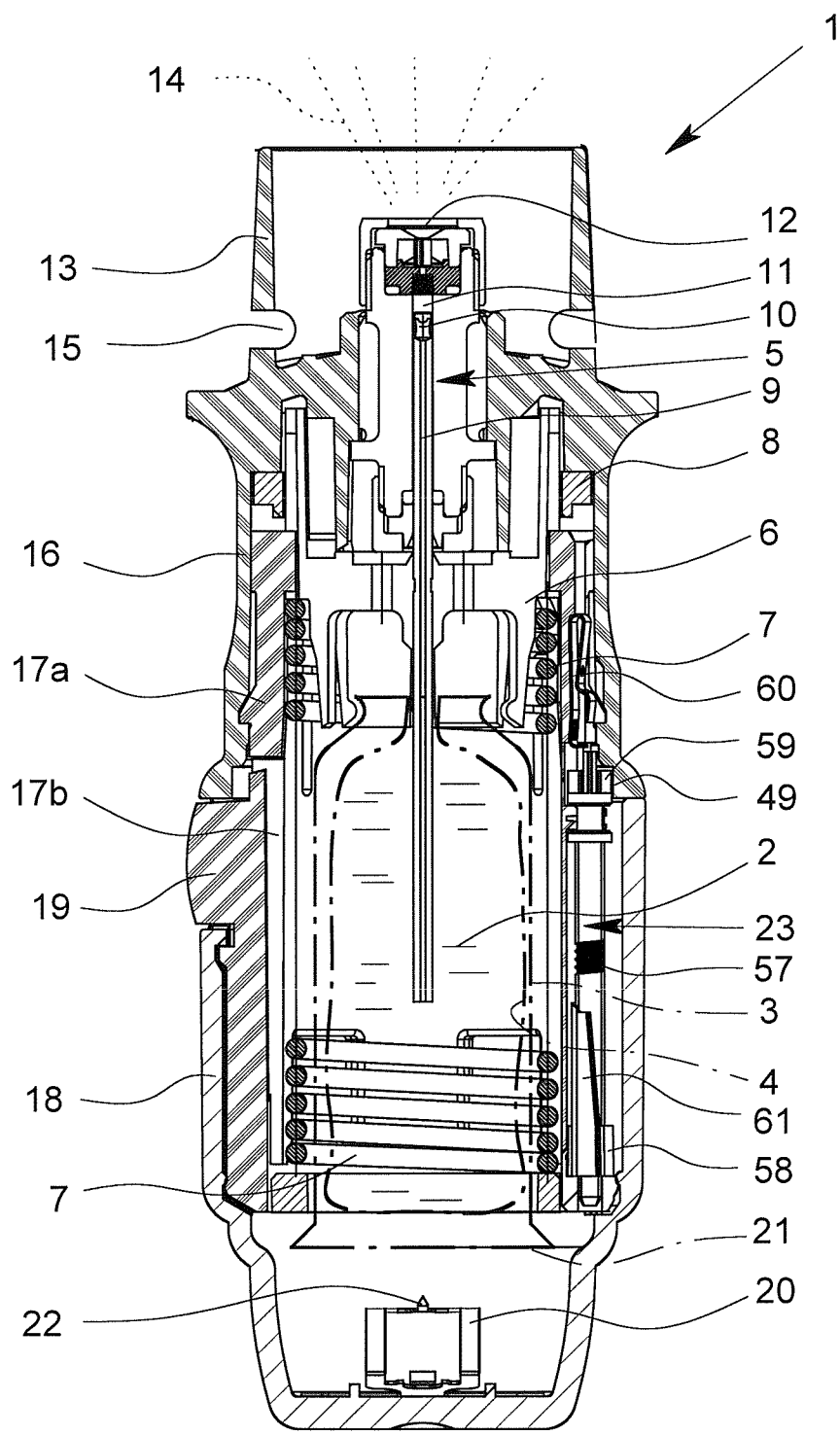

(51) Int. Cl.
  *B05B 11/00* (2006.01)
  *G06M 1/02* (2006.01)
  *G06M 1/24* (2006.01)
  *A61M 11/00* (2006.01)

(52) U.S. Cl.
  CPC ........ *B05B 11/0054* (2013.01); *B05B 11/308* (2013.01); *B05B 11/3091* (2013.01); *G06M 1/026* (2013.01); *G06M 1/24* (2013.01); *A61M 2205/273* (2013.01); *F04C 2270/0421* (2013.01)

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,354,883 A | 11/1967 | Southerland |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Fedit |
| 3,580,249 A | 5/1971 | Takaoka |
| 3,590,557 A | 7/1971 | Vogel |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,802,604 A | 4/1974 | Morane et al. |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,120,995 A | 10/1978 | Phipps et al. |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,456,016 A | 6/1984 | Nowacki et al. |
| 4,467,965 A | 8/1984 | Skinner |
| 4,476,116 A | 10/1984 | Anik |
| 4,515,586 A | 5/1985 | Mendenhall et al. |
| 4,516,967 A | 5/1985 | Kopfer |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lerner |
| 4,973,318 A | 11/1990 | Holm et al. |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,584,285 A | 12/1996 | Salter et al. |
| 5,593,069 A | 1/1997 | Jinks |
| 5,599,297 A | 2/1997 | Chin et al. |
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |

(56) References Cited

U.S. PATENT DOCUMENTS

| | | |
|---|---|---|
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,777 A | 3/2000 | Faithfull et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,109,479 A | 8/2000 | Ruckdeschel |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A * | 11/2000 | Cirrillo .............. A61M 15/0065 128/203.15 |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,336,453 B1 | 1/2002 | Scarrott et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | van der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Oechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,446,054 B1 | 9/2002 | Mayorga Lopez |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |

(56) References Cited

U.S. PATENT DOCUMENTS

| | | |
|---|---|---|
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,167,171 B2 | 5/2012 | Moretti |
| 8,298,622 B2 | 10/2012 | Nakayama et al. |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 * | 2/2014 | Leak et al. ............... 222/309 |
| 8,656,910 B2 | 2/2014 | Boeck et al. |
| 8,733,341 B2 | 5/2014 | Boeck et al. |
| 8,734,392 B2 | 5/2014 | Stadelhofer |
| 8,950,393 B2 | 2/2015 | Holakovsky et al. |
| 8,960,188 B2 | 2/2015 | Bach et al. |
| 8,997,735 B2 | 4/2015 | Zierenberg et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 * | 1/2002 | Schuler et al. ......... 128/200.14 |
| 2002/0005195 A1 | 1/2002 | Shick et al. |
| 2002/0007155 A1 | 1/2002 | Freund et al. |
| 2002/0046751 A1 | 4/2002 | MacRae et al. |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0130195 A1 * | 9/2002 | Jaeger ............... A61M 15/0065 239/333 |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0183225 A1 | 10/2003 | Knudsen |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0196660 A1 | 10/2003 | Haveri |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 * | 5/2004 | Schyra ................. A61M 15/00 128/200.14 |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0164186 A1 | 8/2004 | Kladders et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0210199 A1 | 10/2004 | Atterbury et al. |
| 2004/0231667 A1 | 11/2004 | Horton et al. |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239886 A1 | 10/2006 | Nakayama et al. |
| 2006/0239930 A1 | 10/2006 | Lamche et al. |
| 2006/0254579 A1 | 11/2006 | Grychowski et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 * | 3/2007 | Geser et al. ............. 128/200.14 |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0264437 A1 | 11/2007 | Zimmermann et al. |
| 2007/0272763 A1 | 11/2007 | Dunne et al. |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0060640 A1 | 3/2008 | Waldner et al. |
| 2008/0083408 A1 | 4/2008 | Hodson et al. |
| 2008/0092885 A1 | 4/2008 | von Schuckmann |
| 2008/0156321 A1 | 7/2008 | Bowman et al. |
| 2008/0197045 A1 | 8/2008 | Metzger et al. |
| 2008/0249459 A1 | 10/2008 | Godfrey et al. |
| 2008/0264412 A1 | 10/2008 | Meyer et al. |
| 2008/0265198 A1 | 10/2008 | Warby |
| 2008/0283553 A1 | 11/2008 | Cox et al. |
| 2008/0299049 A1 | 12/2008 | Stangl |
| 2008/0308580 A1 * | 12/2008 | Gaydos et al. ............... 222/333 |
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0211576 A1 * | 8/2009 | Lehtonen ............... A61M 15/00 128/203.12 |
| 2009/0221626 A1 | 9/2009 | Schmidt |
| 2009/0235924 A1 | 9/2009 | Holakovsky et al. |
| 2009/0272664 A1 | 11/2009 | Marshall et al. |

(56) References Cited

U.S. PATENT DOCUMENTS

| | | |
|---|---|---|
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2010/0313884 A1 | 12/2010 | Elliman |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0245780 A1 | 10/2011 | Helmer et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0114387 A1 | 4/2015 | Bach et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320947 A1 | 11/2015 | Eicher et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497059 A1 | 3/2004 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0811430 A1 | 3/1997 |
| EP | 0778221 A1 | 6/1997 |
| EP | 0845253 A2 | 6/1998 |
| EP | 0845265 | 6/1998 |
| EP | 0860210 A2 | 8/1998 |
| EP | 09146428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1978 |
| GB | 2081396 A | 2/1982 |
| GB | 2101020 A | 1/1983 |
| GB | 2279273 A | 1/1995 |
| GB | 2291135 A | 1/1996 |
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |

(56) References Cited

FOREIGN PATENT DOCUMENTS

| | | |
|---|---|---|
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2002235940 A | 8/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 8100674 A1 | 3/1981 |
| WO | 8200785 A1 | 3/1982 |
| WO | 8300288 A1 | 2/1983 |
| WO | 8303054 A1 | 9/1983 |
| WO | 8605419 A1 | 9/1986 |
| WO | 8706137 A1 | 10/1987 |
| WO | 8803419 A1 | 5/1988 |
| WO | 8900889 A1 | 2/1989 |
| WO | 8900947 A1 | 2/1989 |
| WO | 8902279 A1 | 3/1989 |
| WO | 8903672 A1 | 5/1989 |
| WO | 8903673 A1 | 5/1989 |
| WO | 8905139 A1 | 6/1989 |
| WO | 9009780 A1 | 9/1990 |
| WO | 9009781 A1 | 9/1990 |
| WO | 9114468 A1 | 10/1991 |
| WO | 9206704 A1 | 4/1992 |
| WO | 9217231 A1 | 10/1992 |
| WO | 9221332 A1 | 12/1992 |
| WO | 9222286 | 12/1992 |
| WO | 9313737 A1 | 7/1993 |
| WO | 9324164 A1 | 12/1993 |
| WO | 9325321 A1 | 12/1993 |
| WO | 9407607 A1 | 4/1994 |
| WO | 9417822 A1 | 8/1994 |
| WO | 9425371 A1 | 11/1994 |
| WO | 9427653 A2 | 12/1994 |
| WO | 9503034 A1 | 2/1995 |
| WO | 9532015 A1 | 11/1995 |
| WO | 9600050 A1 | 1/1996 |
| WO | 9606011 A2 | 2/1996 |
| WO | 9606581 A1 | 3/1996 |
| WO | 9623522 A1 | 8/1996 |
| WO | 9701329 A1 | 1/1997 |
| WO | 9706813 A1 | 2/1997 |
| WO | 9706842 A1 | 2/1997 |
| WO | 9712683 A1 | 4/1997 |
| WO | 9712687 A1 | 4/1997 |
| WO | 9720590 A1 | 6/1997 |
| WO | 9723208 A1 | 7/1997 |
| WO | 9727804 A1 | 8/1997 |
| WO | 9735562 A1 | 10/1997 |
| WO | 9741833 A1 | 11/1997 |
| WO | 9812511 A2 | 3/1998 |
| WO | 9827959 A2 | 7/1998 |
| WO | 9831346 A1 | 7/1998 |
| WO | 9839043 A1 | 9/1998 |
| WO | 9901227 A1 | 1/1999 |
| WO | 9907340 A1 | 2/1999 |
| WO | 9911563 A1 | 3/1999 |
| WO | 9916530 A1 | 4/1999 |
| WO | 9943571 A1 | 9/1999 |
| WO | 9962495 A2 | 12/1999 |
| WO | 9965464 | 12/1999 |
| WO | 0001612 A2 | 1/2000 |
| WO | 0023037 A1 | 4/2000 |
| WO | 0023065 A2 | 4/2000 |
| WO | 0027543 A1 | 5/2000 |
| WO | 0033965 A1 | 6/2000 |
| WO | 0037336 A1 | 6/2000 |
| WO | 0049988 A2 | 8/2000 |
| WO | 0064779 A1 | 11/2000 |
| WO | 0113885 A1 | 3/2001 |
| WO | 0128489 A1 | 4/2001 |
| WO | 0164182 A2 | 9/2001 |
| WO | 0185097 A2 | 11/2001 |
| WO | 0187392 A2 | 11/2001 |
| WO | 0197888 A2 | 12/2001 |
| WO | 0198175 A1 | 12/2001 |
| WO | 0198176 A2 | 12/2001 |
| WO | 0204054 A1 | 1/2002 |
| WO | 0205879 A1 | 1/2002 |
| WO | 0217988 A2 | 3/2002 |
| WO | 0232899 A1 | 4/2002 |
| WO | 0234411 A1 | 5/2002 |
| WO | 02070141 A1 | 9/2002 |
| WO | 02089887 A1 | 11/2002 |
| WO | 03002045 A1 | 1/2003 |
| WO | 03014832 A1 | 2/2003 |
| WO | 03020253 A2 | 3/2003 |
| WO | 03022332 A2 | 3/2003 |
| WO | 03035030 A1 | 5/2003 |
| WO | 03037159 A2 | 5/2003 |
| WO | 03037259 A2 | 5/2003 |
| WO | 03049786 A2 | 6/2003 |
| WO | 03050031 A1 | 6/2003 |
| WO | 03053350 A2 | 7/2003 |
| WO | 03057593 A1 | 7/2003 |
| WO | 03059547 A1 | 7/2003 |
| WO | 03068299 A1 | 8/2003 |
| WO | 03087097 A1 | 10/2003 |
| WO | 03097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 2004033954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2004098795 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A1 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |

(56) References Cited

FOREIGN PATENT DOCUMENTS

| | | | |
|---|---|---|---|
| WO | 2007030162 | A2 | 3/2007 |
| WO | 2007049239 | A2 | 5/2007 |
| WO | 2007060104 | A2 | 5/2007 |
| WO | 2007060105 | A1 | 5/2007 |
| WO | 2007060106 | A1 | 5/2007 |
| WO | 2007060107 | A1 | 5/2007 |
| WO | 2007060108 | A2 | 5/2007 |
| WO | 2007062721 | A1 | 6/2007 |
| WO | 2007090822 | A2 | 8/2007 |
| WO | 2007101557 | A2 | 9/2007 |
| WO | 2007128381 | A1 | 11/2007 |
| WO | 2007134965 | A1 | 11/2007 |
| WO | 2007134966 | A1 | 11/2007 |
| WO | 2007134967 | A1 | 11/2007 |
| WO | 2007134968 | A1 | 11/2007 |
| WO | 2007141201 | A1 | 12/2007 |
| WO | 2007141203 | A1 | 12/2007 |
| WO | 2008023017 | A2 | 2/2008 |
| WO | 2008047035 | A2 | 4/2008 |
| WO | 2008077623 | A1 | 7/2008 |
| WO | 2008124666 | A2 | 10/2008 |
| WO | 2008138936 | A1 | 11/2008 |
| WO | 2008146025 | A2 | 12/2008 |
| WO | 2009006137 | A1 | 1/2009 |
| WO | 2009047021 | A1 | 4/2009 |
| WO | 2009047173 | A2 | 4/2009 |
| WO | 2009050978 | A1 | 4/2009 |
| WO | 2009090245 | A1 | 7/2009 |
| WO | 2009103510 | A1 | 8/2009 |
| WO | 2009115200 | A1 | 9/2009 |
| WO | 2010005946 | A2 | 1/2010 |
| WO | 2010006870 | A1 | 1/2010 |
| WO | 2010094305 | A1 | 8/2010 |
| WO | 2010094413 | A2 | 8/2010 |
| WO | 2010112358 | A2 | 10/2010 |
| WO | 2010133294 | A2 | 11/2010 |
| WO | 2011006711 | A1 | 1/2011 |
| WO | 2011064160 | A1 | 6/2011 |
| WO | 2011064163 | A1 | 6/2011 |
| WO | 2011064164 | A1 | 6/2011 |
| WO | 2011131779 | A1 | 10/2011 |
| WO | 2011154295 | A2 | 12/2011 |
| WO | 2011160932 | A1 | 12/2011 |
| WO | 2012130757 | A1 | 10/2012 |
| WO | 2012159914 | A1 | 11/2012 |
| WO | 2012160047 | A2 | 11/2012 |
| WO | 2012160052 | A1 | 11/2012 |
| WO | 2012161685 | A1 | 11/2012 |
| WO | 2012162305 | A1 | 11/2012 |
| WO | 2013110601 | A1 | 8/2013 |
| WO | 2013152861 | A1 | 10/2013 |
| WO | 2013152894 | A1 | 10/2013 |
| WO | 2015018901 | A1 | 2/2015 |
| WO | 2015018903 | A1 | 2/2015 |
| WO | 2015018904 | A1 | 2/2015 |
| WO | 2015169431 | A2 | 11/2015 |
| WO | 2015169732 | A1 | 11/2015 |
| ZA | 199901520 | A | 12/1999 |

OTHER PUBLICATIONS

"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226, 1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrated Drugs via a SERS Microfluidic System; ChemPhysChem; 2007; vol. 8; No. 18; pp. 2665-2670.
Bocci et al., "Pulmonary catabolism of interferons: alveolar absorption of 125I-labeled human interferon alpha is accompanied by partial loss of biological activity". Antiviral Research, vol. 4, 1984, pp. 211-220.
Chen, F-K et al., "A study of forming pressure in the tube-hydroforming process". Journal of Materials Processing Technology, 192-193, 2007, p. 404-409.
China Suppliers, Shanghai Lite Chemical Technology Co., Ltd. Product details on polyvinylpyrrolidones. Obtained online by the USPTO examiner on Apr. 24, 2011.
Cras et al., "Comparison of chemical cleaning methods of glass in preparation for silanization". Biosensors & Bioelectronics, vol. 14, 1999, pp. 683-688.
Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlag Berlin Heidelberg, 2001, 4 pages.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.
Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.
International Search Report and Written Opinion for PCT/EP04006768 dated Sep. 24, 2004.
International Search Report and Written Opinion for PCT/EP2005/001947 dated May 19, 2005.
International Search Report and Written Opinion for PCT/EP2005/004792 dated Aug. 4, 2015.
International Search Report and Written Opinion for PCT/EP2005/055560 dated Mar. 2, 2006.
International Search Report and Written Opinion for PCT/EP2005/068399 dated Jun. 25, 2007.
International Search Report and Written Opinion for PCT/EP2006/068395 dated Jun. 25, 2007.
International Search Report and Written Opinion for PCT/EP2006/068396 dated Apr. 23, 2007.
International Search Report and Written Opinion for PCT/EP2006/068397 dated Feb. 21, 2007.
International Search Report and Written Opinion for PCT/EP2006/068398 dated May 10, 2007.
International Search Report and Written Opinion for PCT/EP2007/001558 dated Sep. 28, 2007.
International Search Report and Written Opinion for PCT/EP2007/054492 dated Aug. 16, 2007.
International Search Report and Written Opinion for PCT/EP2007/055381 dated Sep. 3, 2007.

(56) References Cited

OTHER PUBLICATIONS

International Search Report and Written Opinion for PCT/EP2007/055383 dated Sep. 27, 2007.
International Search Report and Written Opinion for PCT/EP2009/001619 dated Jun. 10, 2009.
International Search Report and Written Opinion for PCT/EP2009/005949 dated Jan. 20, 2010.
International Search Report and Written Opinion for PCT/EP2010/057937 dated Jul. 20, 2010.
International Search Report and Written Opinion for PCT/EP2012/058905 dated Oct. 19, 2012.
International Search Report and Written Opinion for PCT/EP2012/059454 dated Jan. 14, 2013.
Abstract in English for WO2009050978, 2009.
International Search Report and Written Opinion for PCT/EP2014/067001 dated Sep. 9, 2014.
International Search Report and Written Opinion for PCT/EP2014/067004 dated Jan. 10, 2014.
International Search Report and Written Opinion for PCT/EP2014/067006 dated Nov. 24, 2014.
International Search Report for corresponding PCT/EP2010/000796; dated Oct. 28, 2010.
International Search Report for PCT/EP199804803 dated Dec. 15, 1998.
International Search Report for PCT/EP1999/07589 dated Mar. 1, 2000.
International Search Report for PCT/EP2007/003322 dated Aug. 17, 2007.
International Search Report for PCT/EP2007/054489 dated Feb. 10, 2007.
International Search Report for PCT/EP2008/055863 dated Dec. 19, 2008.
International Search Report for PCT/EP2009/001619 dated Jun. 10, 2009.
International Search Report for PCT/EP2010/002740 dated Nov. 12, 2010.
International Search Report for PCT/EP2010/053668; dated Nov. 8, 2010.
International Search Report PCT/EP2007/051095 dated Sep. 21, 2007.
Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.
Jendle et al., "Intrapulmonary administration of insulin to healthy volunteers". Journal of Internal Medicine, vol. 240, 1996, pp. 93-98.
Kutchoukov et al., "Fabrication of nanofluidic devices using glass-to-glass anodic bonding" Sensors and Actuators A, vol. 114, 2004, pp. 521-527.
Lougheed et al., "Insulin Aggregation in Artificial Delivery Systems". Diabetologia, vol. 19, 1980, pp. 1-9.
Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).

Niven et al., "Some Factors Associated with the Ultrasonic Nebulization of Proteins". Pharmaceutical Research, vol. 12, No. 1, 1995, pp. 53-59.
Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.
Trasch et al., "Performance data of refloquant Glucose in the Evaluation of Reflotron". Clinical Chemistry, vol. 30, 1984, p. 969 (abstract only).
Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.
Wang et al.; Self-Assembled Silane Monolayers: Fabrication with Nanoscale Uniformity; Langmuir; 2005; vol. 21; No. 5; pp. 1848-1857.
International Search Report and Written Opinion for PCT/EP2013/001068 dated Jun. 5, 2013.
International Search Report for PCT/EP2008/011112 dated Sep. 3, 2009.
International Search Report for PCT/EP2009/001153; dated May 20, 2009.
Abstract in English of FR2604363, Sep. 30, 1986.
International Search Report and Written Opinion for PCT/EP2010/067896, dated Apr. 13, 2011.
International Search Report and Written Opinion for PCT/EP2010/067902 dated May 2, 2011.
International Search Report for PCT/EP2012/055209 dated Jan. 6, 2012.
International Search Report and Written Opinion for PCT/EP2010/067901, dated Apr. 14, 2011.
"Activate". Collins English Dictionary, London: Collins, 2000, 2 pages. [Retrieved at http://search.credoreference.com/content/entry/hcengdict/activate/0 on Jun. 12, 2014].
International Search Report for PCT/EP2011/059088; dated Sep. 26, 2011.
International Search Report and Written Opinion for PCT/EP2015/000903 dated Nov. 5, 2015.
International Search Report and Written Opinion for PCT/EP2015/059691 dated Oct. 8, 2015.
Beasley R et al: "Preservatives in Nebulizer solutions: Risks without Benefit" Pharmacotherapy, Boston, US, Bd. 18, Nr. 1, Jan. 1998, pp. 130-139.
International Search Report and Written Opinion for PCT/EP2007/054488 dated Jul. 18, 2007.
International Search Report and Written Opinion for PCT/EP2007/054490 dated Jul. 17, 2007.
Beasley R et al: "Preservatives in Nebulizer solutions: Risks without Benefit" Pharmacotherapy, Boston, US, Bd. 18, Nr. 1, Jan. 1998.
JP2005144459—English language abstract only.
International Search Report and Written Opinion for PCT/EP2013/054324 dated Jun. 5, 2013.

* cited by examiner

Prior Art

NEBULIZER

The present invention relates to a nebulizer which is an inhaler for a fluid.

WO 2006/125577 A2 discloses a nebulizer. The nebulizer comprises, as a reservoir for fluid which is to be atomized or nebulizer, an insertable rigid container having an inner bag containing the fluid and a pressure generator with a drive spring for delivering and atomizing the fluid. Preferably, the container is secured against removal. For the purpose, the nebulizer of its housing may be designed such that it can not be opened after the container has been inserted.

Preferably, the container is pre-installed in nebulizer in the delivery state. In particular, the pre-installed container is held by a transportation lock unmovable within the housing in the delivery state in order to avoid any undesired opening of the container.

Before being used for the first time the nebulizer is completely closed. Thus, the pre-installed container is opened by a delivery tube piercing a sealing and a septum to fluidically connect to the inner bag of the container. Further, the transportation lock is opened so that the container can move inside the nebulizer back and forth.

By rotating the lower housing part of the nebulizer the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a locking element the drive spring is released and the fluid in the pressure chamber is put under pressure by the drive spring and is delivered or atomized through a nozzle into a mouthpiece as an aerosol, without the use of propellant gas.

WO 2007/022898 A2 discloses a similar nebulizer. A container can be inserted into a housing of the nebulizer. The housing is closed by a lower or bottom housing part. The container is moving axially forth and back during conveying of the fluid to be nebulized, during pressure generation and/or during nebulization. A counter can be arranged in the housing part. The counter locks the nebulizer against further use if a predetermined number of operations has been reached or exceeded. Then, the housing part may be replaced together with the counter and the container. The container may be connected inseparably with the housing part.

Object of the present invention is to provide a nebulizer with simple assembly or construction.

The above object is achieved by a nebulizer according to claim 1. Preferred embodiments are subject of the subclaims.

According to the present invention, the nebulizer comprises an operation counter counting uses of the nebulizer with the associated container, wherein the operation counter is inseparable from the housing part for replacement together with the container and housing part. The operation counter comprises a first lead screw and an associated, first rider both supported by the housing part. This allows a very simple assembly and/or construction. Further, the known nebulizer can be modified in a relatively simple manner by essentially modifying primarily the replaceable housing part.

Preferably, the operation counter or its rider or an associated opening lock can block opening of the nebulizer or detachment of the housing part and, thus, can block container replacement until a predetermined number of uses has been reached or exceeded with the associated or current container. In addition, the operation counter or its rider can lock the nebulizer against further use, in particular against conveying of fluid into a pressure generator of the nebulizer, tensioning of a drive spring of the nebulizer, rotation of the housing part, pressure generation and/or nebulization, when a predetermined number of uses has been reached or exceeded with the associated or current container. Thus, the operation counter or its rider may provide or control a double-function of the nebulizer. With other words, the operation counter associated to a container controls preferably opening of the nebulizer or container replacement as well as blocking of the nebulizer against further use with the respective container. In the present embodiment, this double-function is achieved or controlled preferably by a common component, here the (first) rider.

Preferably, the container is pre-assembled into the (lower) housing part.

The operation counter can be combined with or used together with a container counter provided at the nebulizer, in particular at an upper part or inner part of the nebulizer.

Preferably, the nebulizer can be used with multiple containers, but is blocked against further use or container replacement after a predetermined number of containers has been inserted and/or used.

Figure 2:
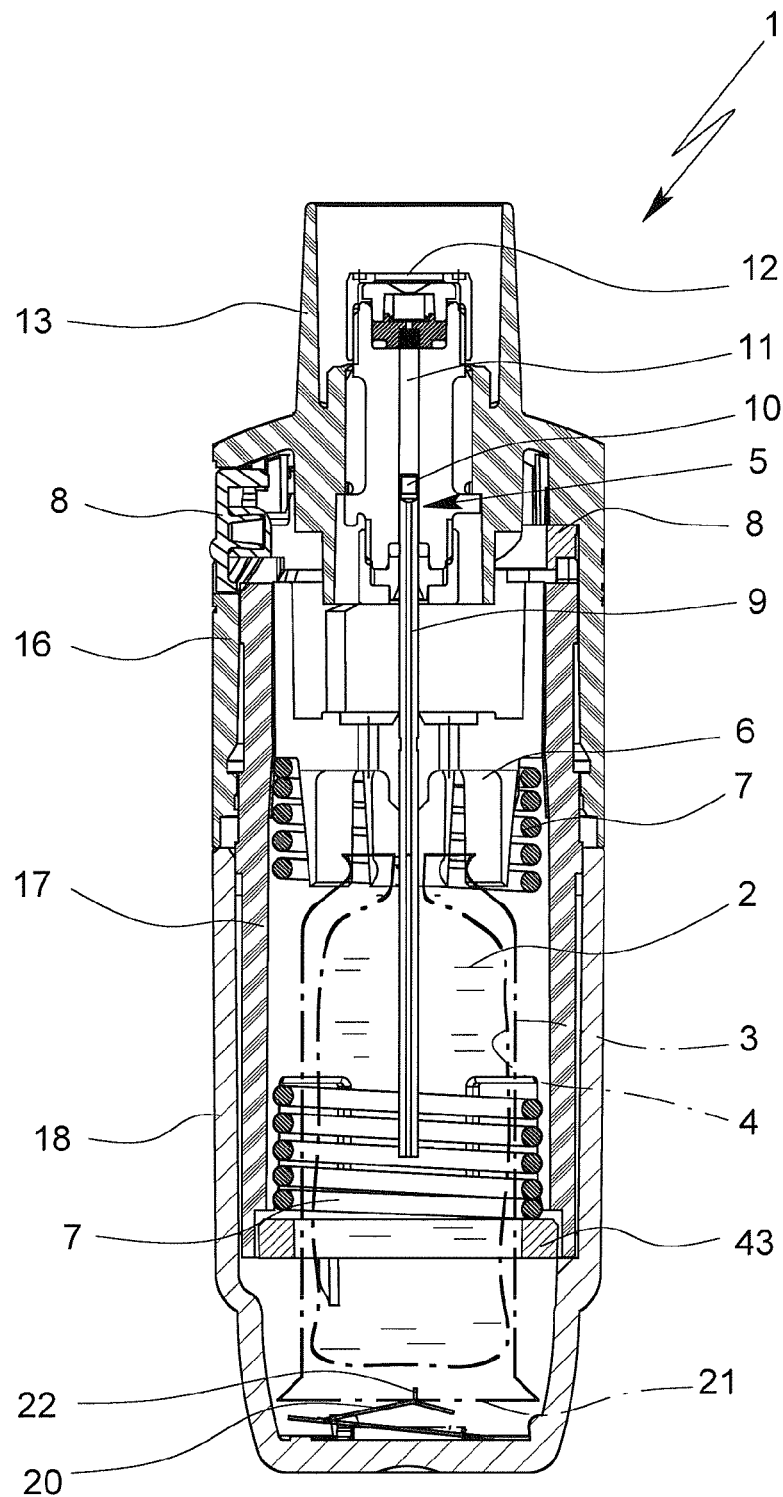
Figure 3:
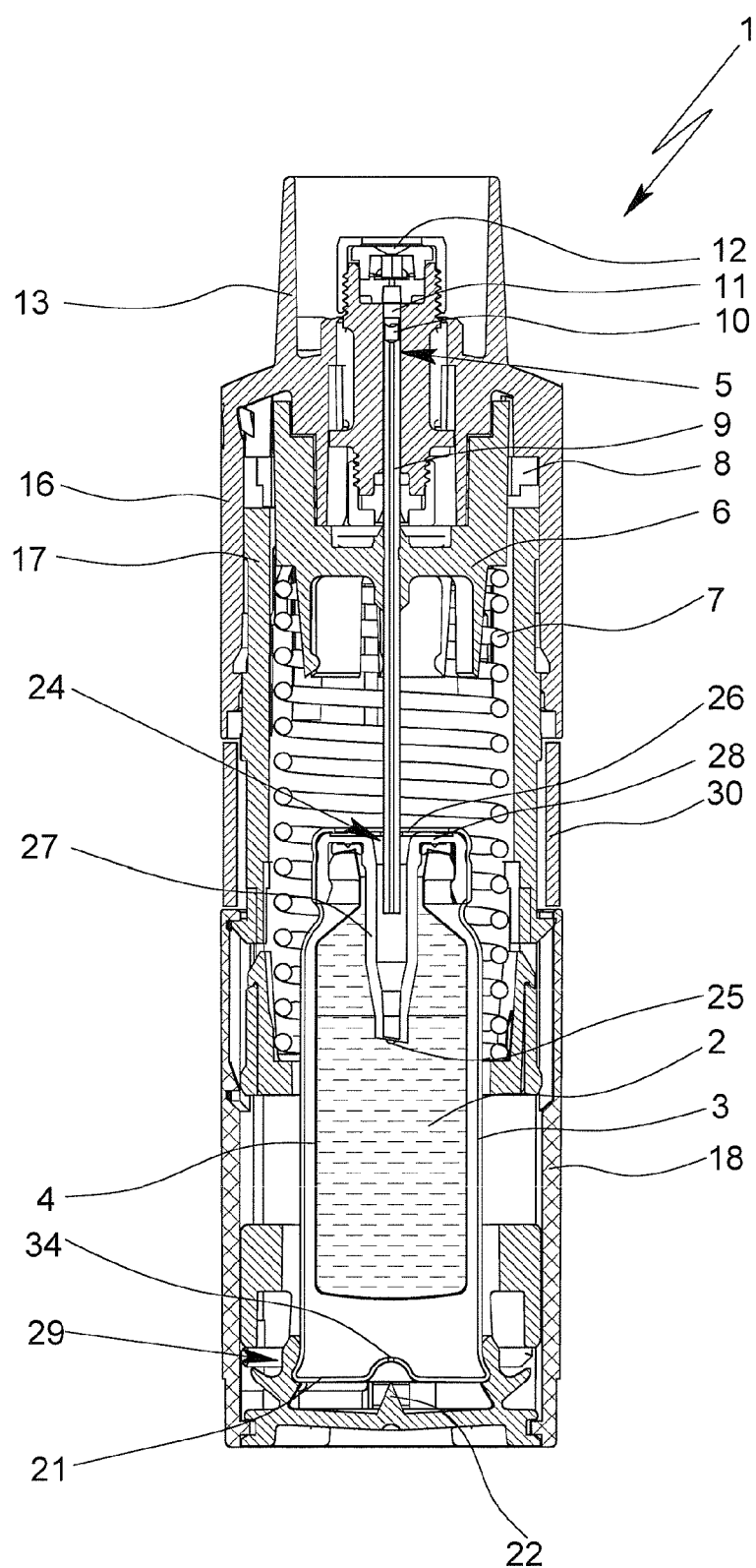
Figure 4:
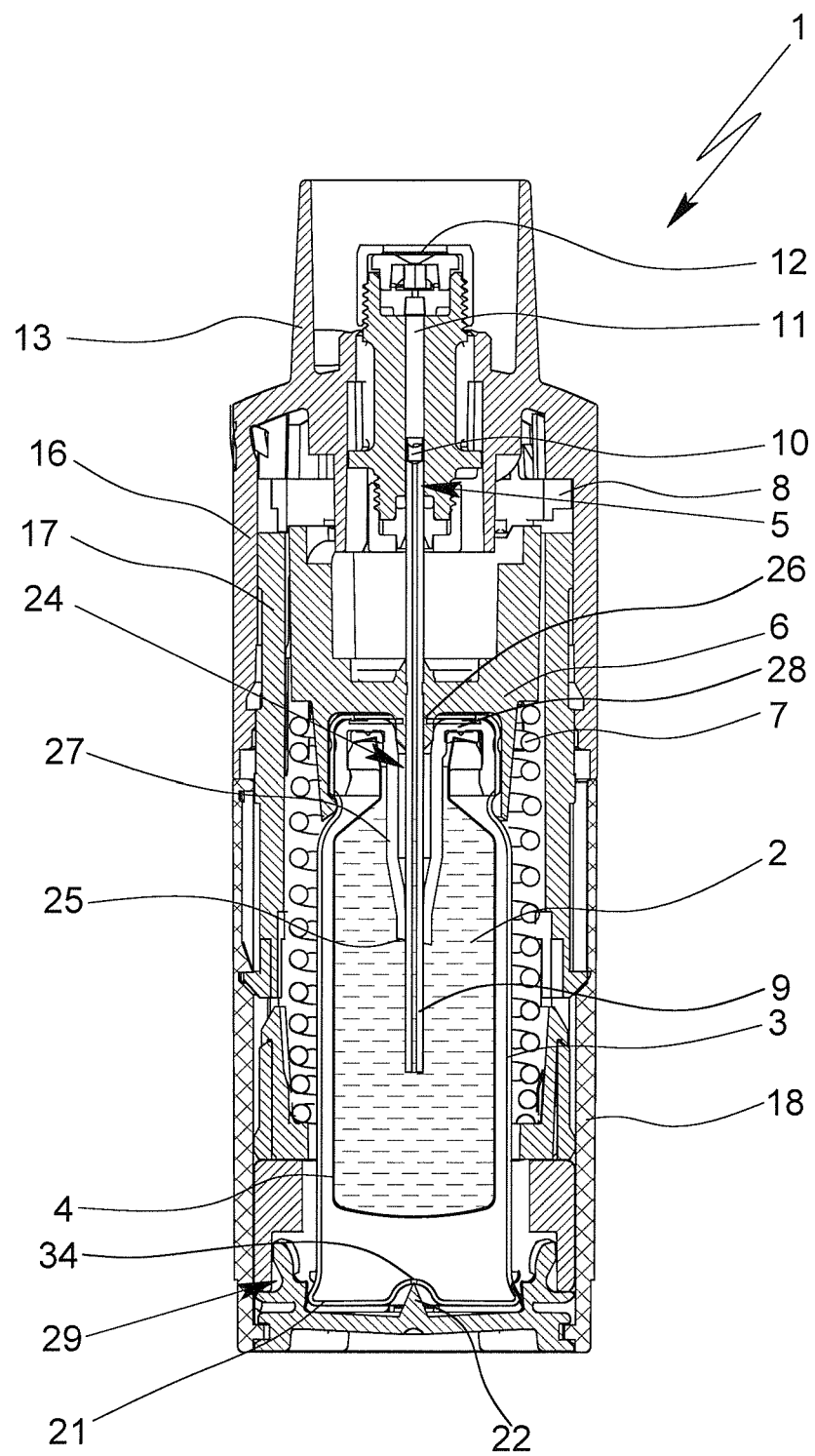
Figure 5:
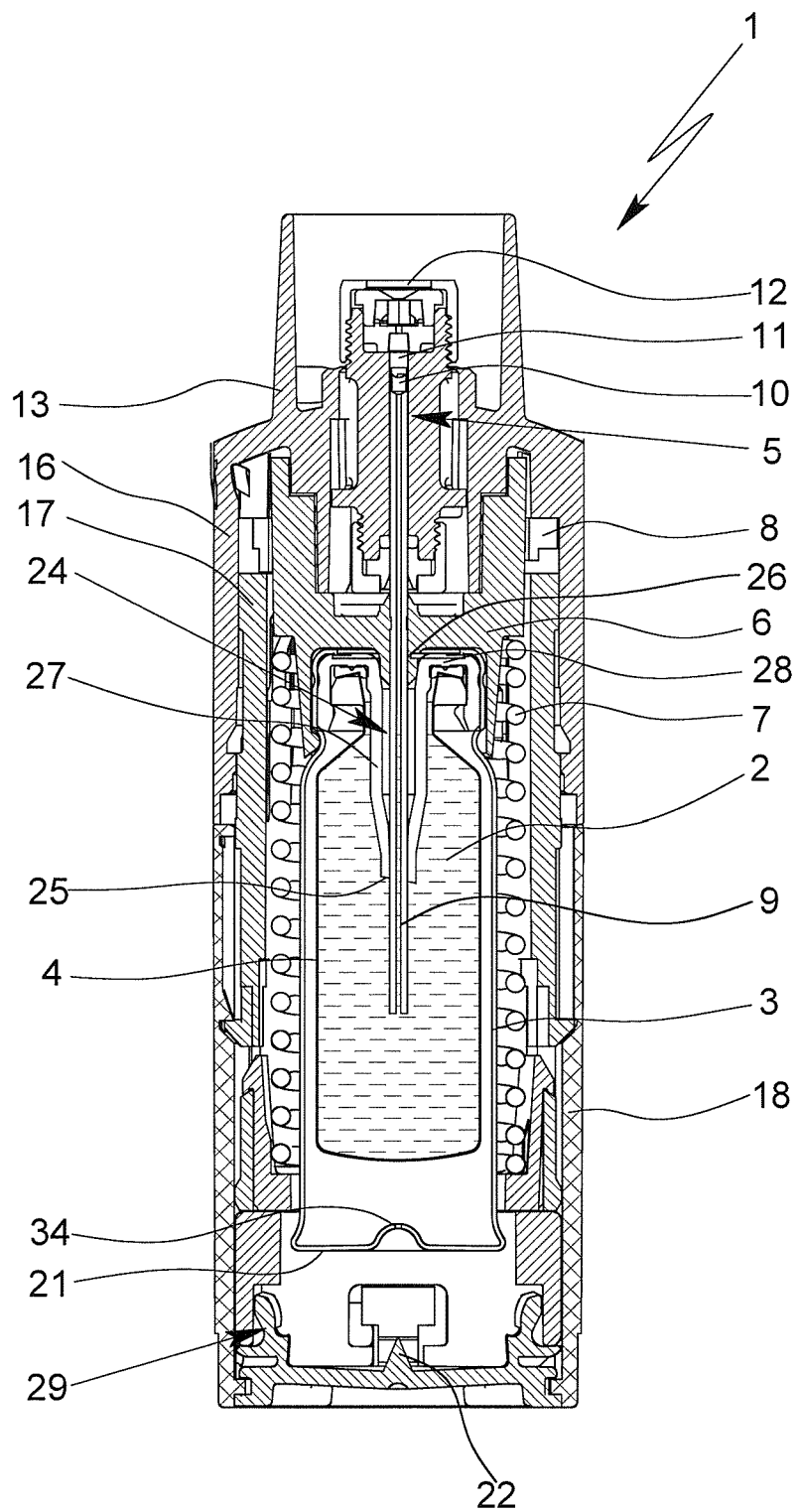
Figure 6:
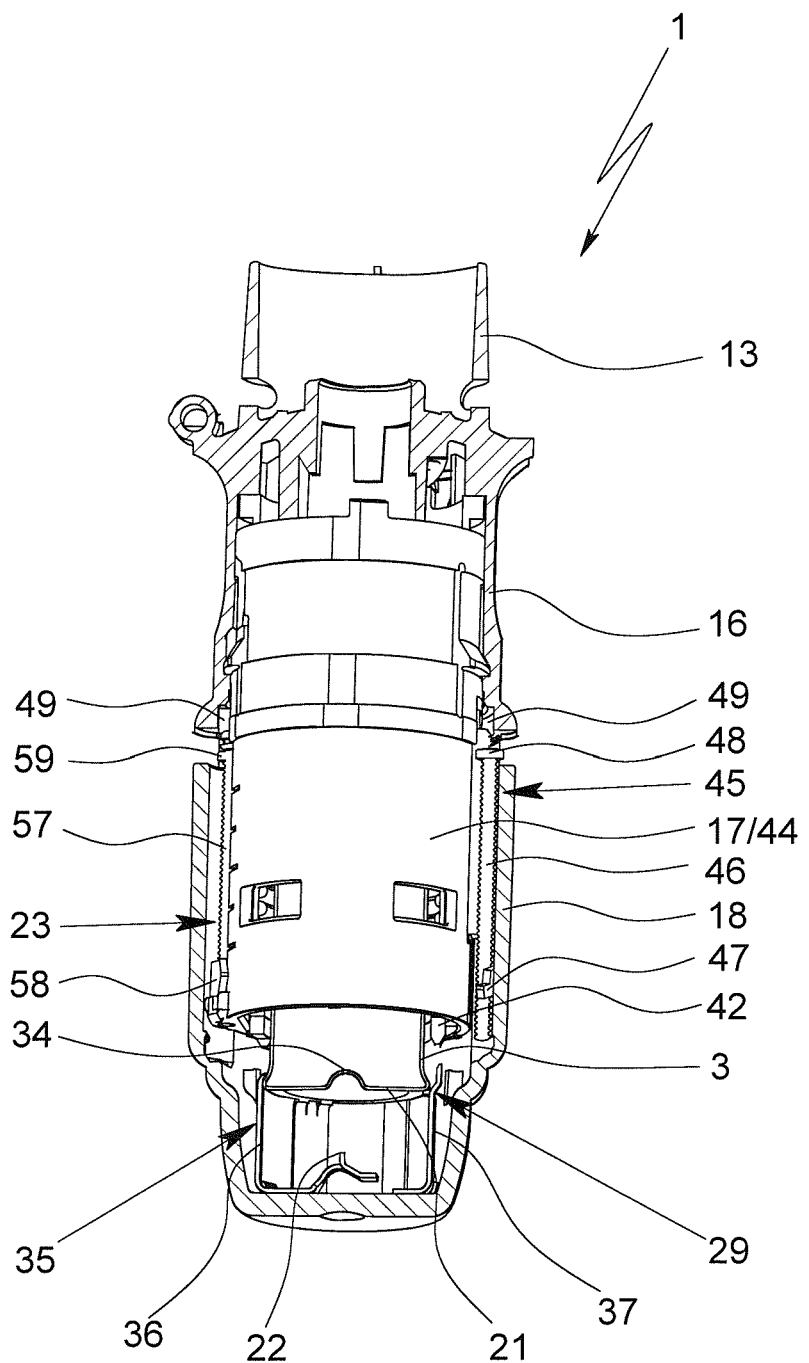
Figure 7:
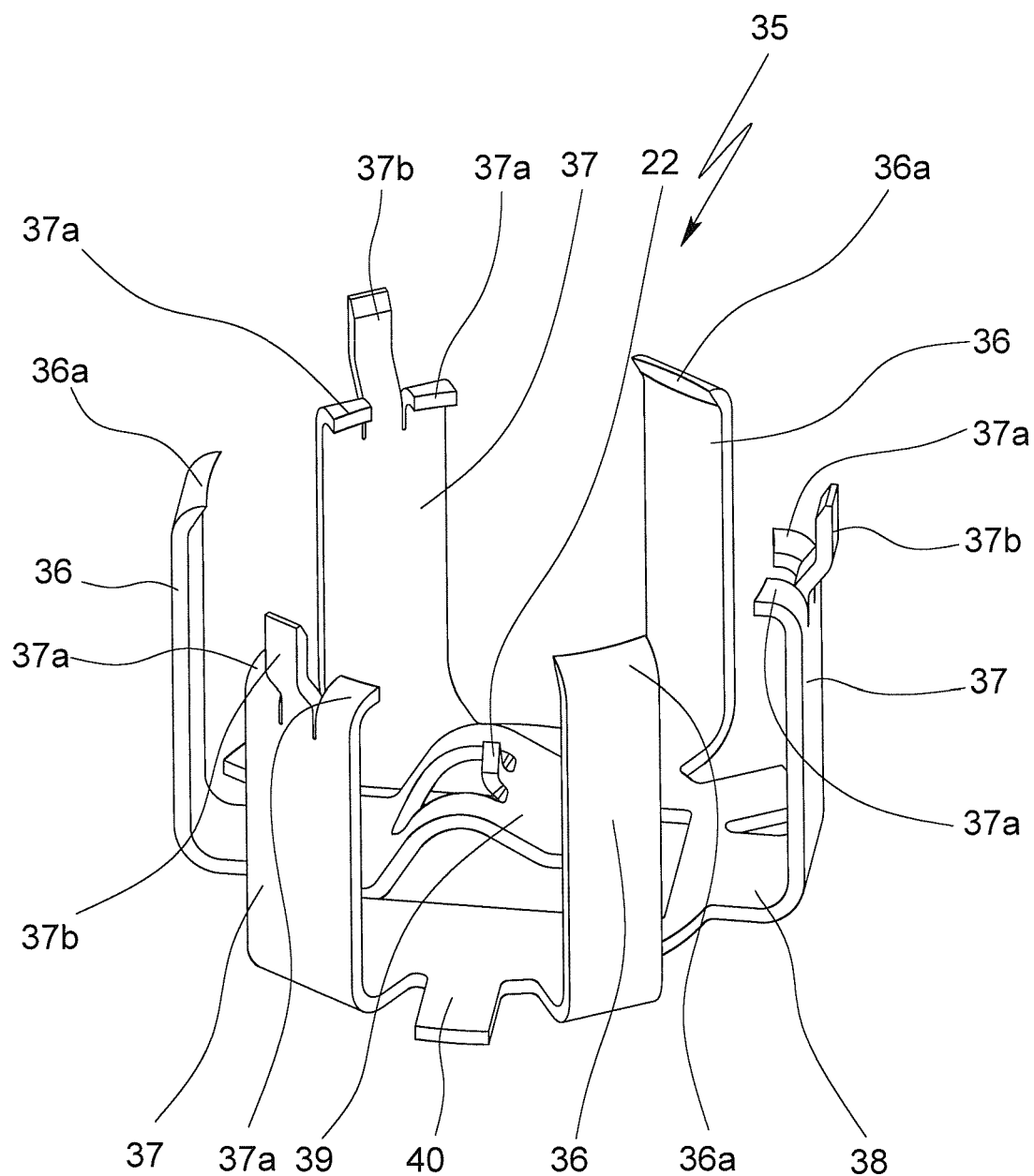
Figure 8:
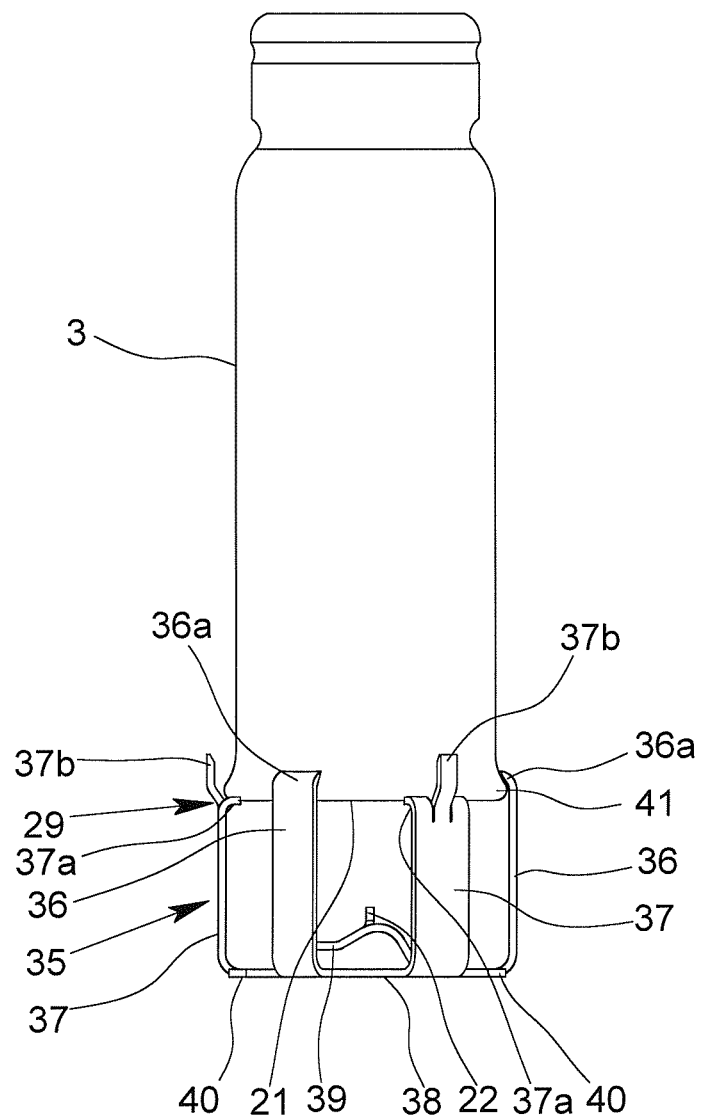
Figure 9:
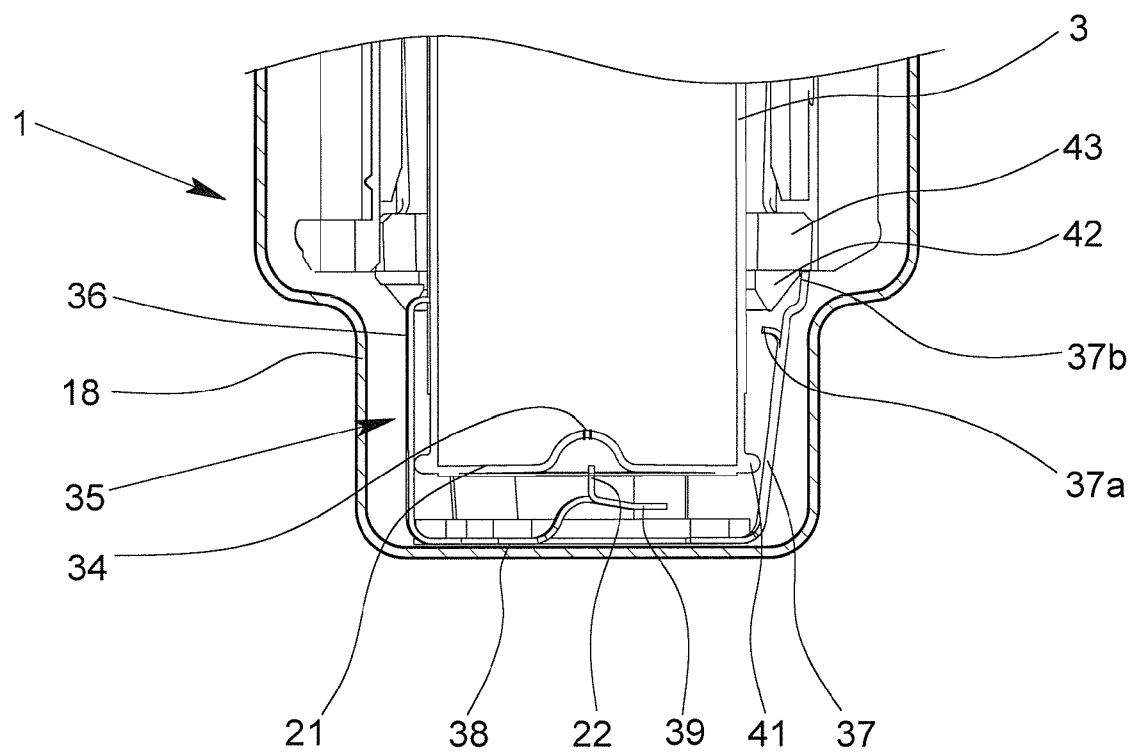
Figure 10:
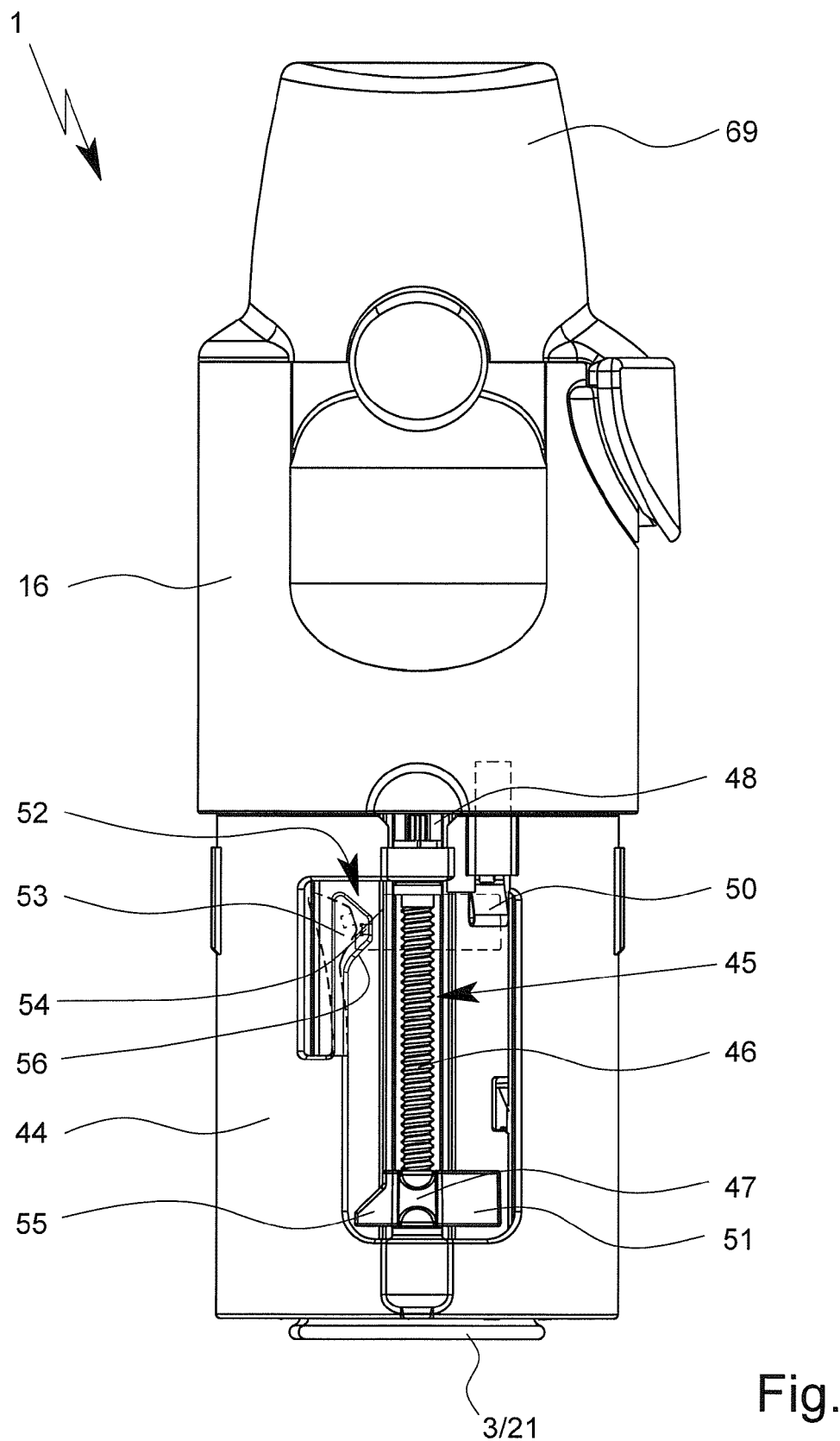
Figure 11:
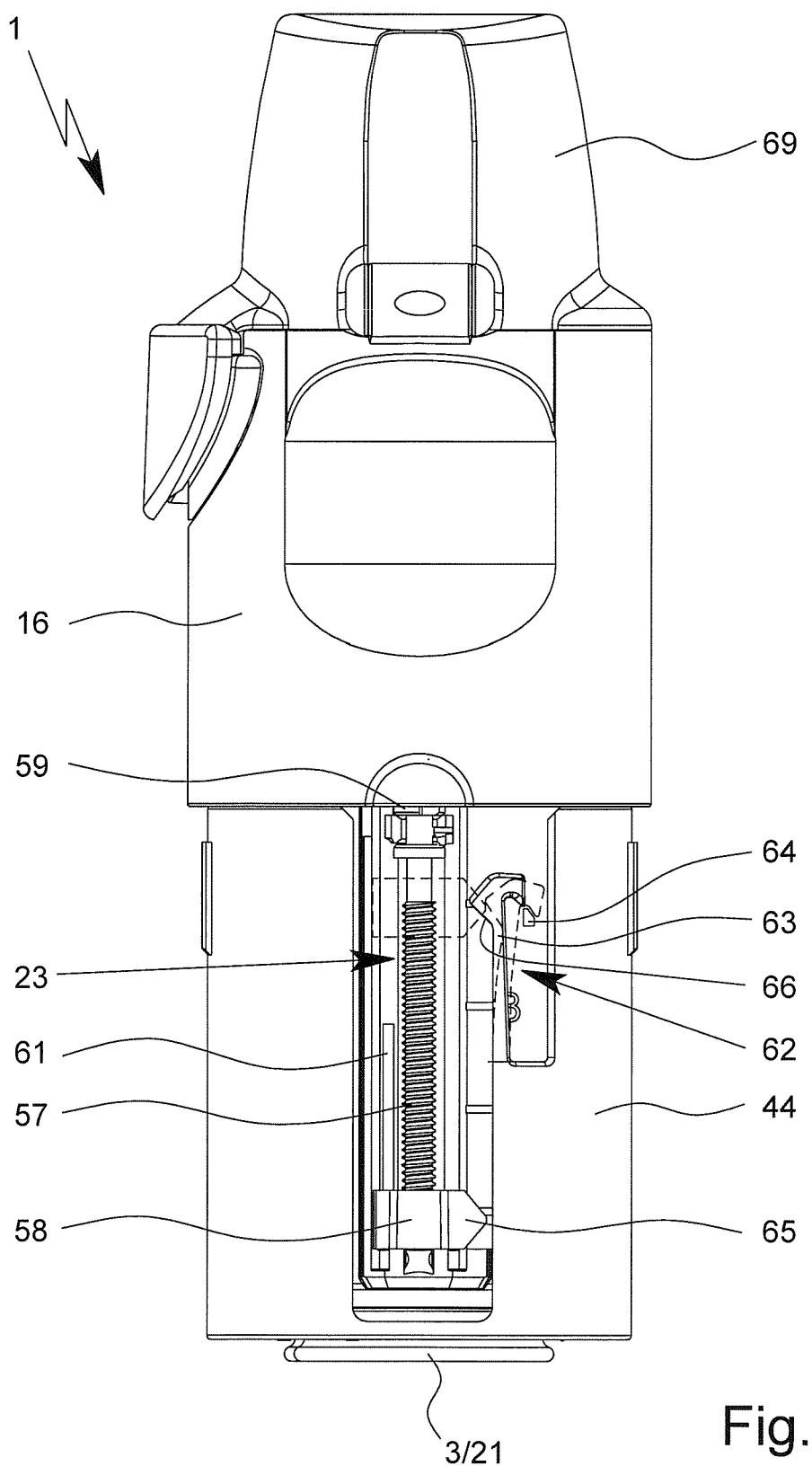
Figure 12:
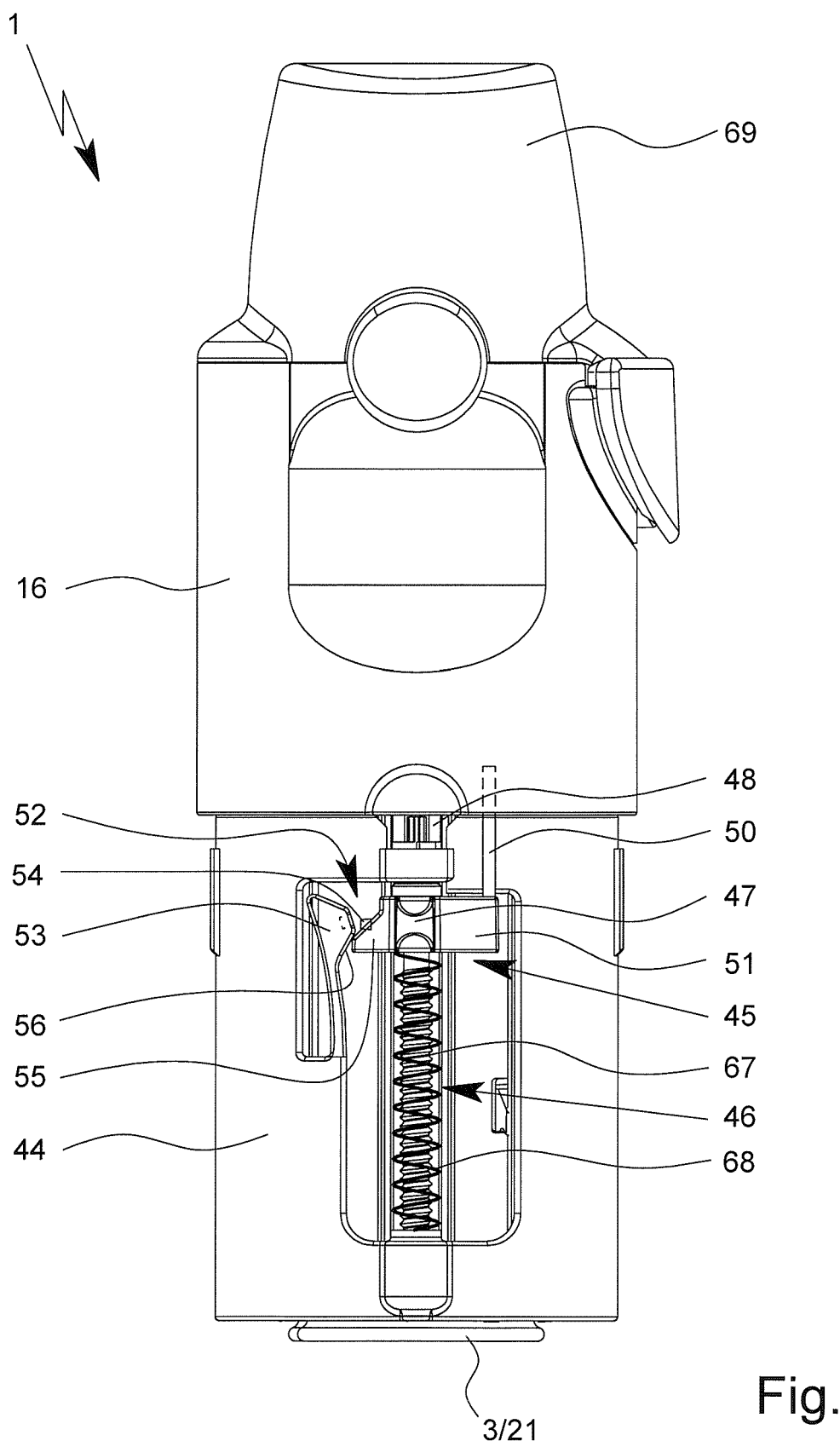
Figure 13:
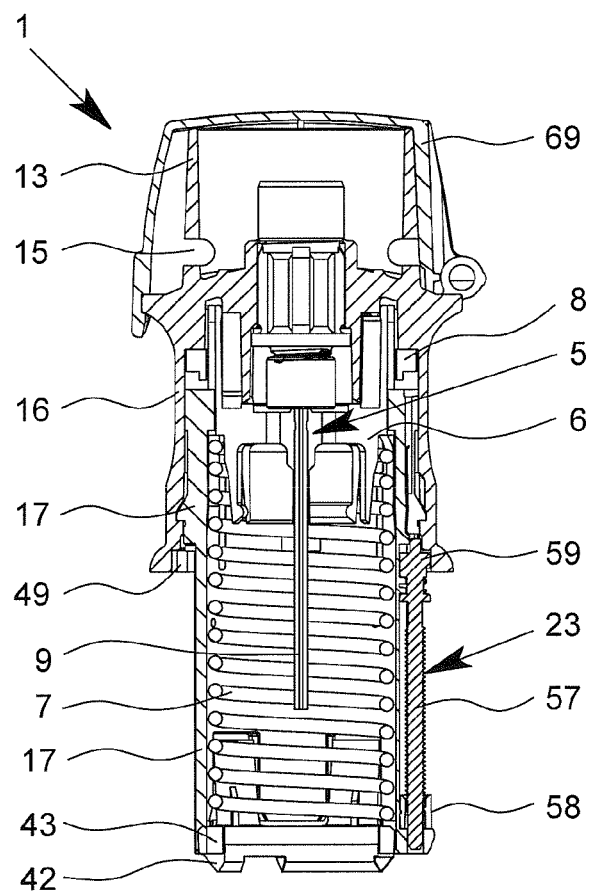
Figure 13:
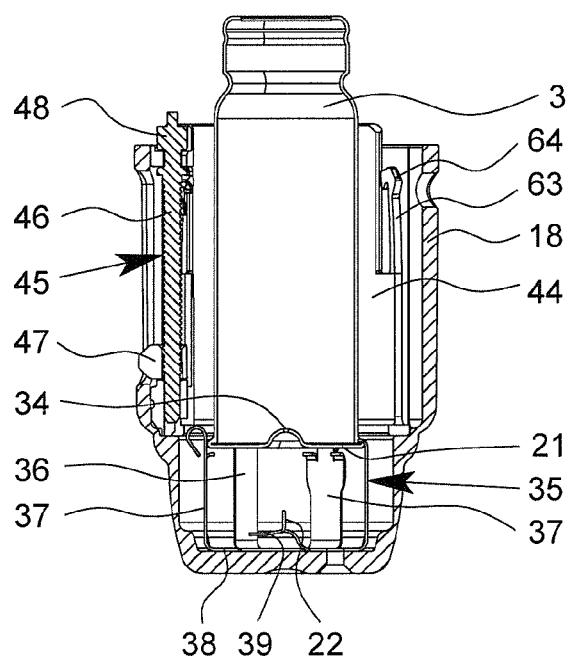

Further advantages, features, characteristics and aspects of the present invention will become apparent from the claims and the following description of preferred embodiments with reference to the drawings. It shows:

FIG. 1 a schematic section of a known nebulizer in a non-tensioned state;

FIG. 2 a schematic section, rotated through 90° compared with FIG. 1, of the known nebulizer in a tensioned state;

FIG. 3 a schematic section of a nebulizer in a delivery state with a partly closed housing and with a pre-installed, closed container;

FIG. 4 a schematic section of the nebulizer according to FIG. 3 in an activated, tensioned state with the completely closed housing and with the opened container;

FIG. 5 a schematic section of the nebulizer according to FIG. 4 in a non-tensioned state;

FIG. 6 a schematic section of a nebulizer according to the present invention with a partly closed housing and with a securing means in a housing part holding unmoveably a container in the nebulizer;

FIG. 7 a perspective view of the securing means;

FIG. 8 a side view of the securing means holding the associated container unmoveably;

FIG. 9 a schematic partial view of a part of the nebulizer with opened securing means so that the container can move;

FIG. 10 a schematic view of an inner member of the nebulizer with an operation counter;

FIG. 11 another schematic view of the inner member with a container counter;

FIG. 12 a schematic view of the inner part member with the operation counter similar to FIG. 10, but according to a modified embodiment; and FIG. 13 a schematic section of the nebulizer with separated housing part and container.

In the Figures, the same reference numerals are used for identical or similar parts, resulting preferably in corresponding or comparable properties and advantages, even if the associated description is not repeated.

FIGS. 1 and 2 show a known nebulizer 1 for atomizing a fluid 2, particularly a highly effective pharmaceutical composition, medicament or the like, diagrammatically shown in a non-tensioned state (FIG.

2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user. Usually the inhaling is done at least once a day, more particularly several times a day, preferably at set intervals, depending on the complain or illness from which a patient is suffering.

The nebulizer 1 is provided with or comprises an insertable or replaceable container 3 containing the fluid 2. The container 3 thus forms a reservoir for the fluid 2, which is to be nebulized. Preferably, the container 3 contains multiple doses of fluid 2 or active substance, in particular sufficient to provide up to 200 dosage units or doses, for example, i.e. to allow up to 200 sprays or applications. A typical container 3, as disclosed in WO 96/06011 A1, holds e.g. a volume of about 2 to 20 ml.

It has to be noted that the dose can vary, in particular depending on the fluid 2 or medicament. The nebulizer 1 can be adapted respectively.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the container 3 can be replaced or exchanged, wherein the number of containers 3, which can be used with the same nebulizer 1, is preferably restricted, e.g. to a total number of four or five containers 3.

The container 3 is preferably substantially cylindrical or cartridge-shaped and once the nebulizer 1 has been opened the container 3 can be inserted therein preferably from below and changed if desired. It is preferably of rigid construction, the fluid 2 in particular being held in a collapsible bag 4 in the container 3.

The nebulizer 1 comprises preferably a pressure generator 5 for conveying and nebulizing the fluid 2, particularly in a preset and optionally in an adjustable dosage amount. The pressure generator 5 comprises preferably a holder 6 for releasable holding the container 3, a drive spring 7 associated to the holder 6, only partly shown, a blocking element 8 which can catch and block the holder 6 and can be manually operated to release the holder 6 allowing drive spring 7 to expand, a conveying element, such as a conveying tube 9, a non-return valve 10, a pressure chamber 11 and/or a nozzle 12 for nebulizing the fluid 2 into a mouthpiece 13. The completely inserted container 3 is fixed or held in the nebulizer 1 via the holder 6 such that the conveying tube 9 penetrates into the container 3. The holder 6 is preferably constructed so that the container 3 can be exchanged.

When the drive spring 7 is axially tensioned in the tensioning process the holder 6 with the container 3 and the conveying tube 9 are moved downwards in the drawings and fluid 2 is sucked out of the container 3 into the pressure chamber 11 of the pressure generator 5 through the non-return valve 10. In this state, the holder 6 is caught by the blocking element 8 so that the drive spring 7 is kept compressed. Then, the nebulizer 1 is in the so-called activated or tensioned state.

During the subsequent relaxation in the nebulization process after actuation or pressing of the blocking element 8 the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2 and/or with a volume of fluid 2 delivered per stroke of 10 to 50 µl, preferably 10 to 20 µl, most preferably about 15 µl. The fluid 2 is converted into or nebulized as aerosol 14 the droplets of which have an aerodynamic diameter of up to 20 µm, preferably 3 to 10 µm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while an air supply can be sucked into the mouthpiece 13 through at least one optional air supply opening 15.

Preferably, the nebulizer 1 or drive spring 7 can be manually activated or tensioned, in particular by actuation of an actuation member.

The nebulizer 1 comprises preferably an upper housing part 16 and an inner part 17 which is rotatable relative thereto (FIG. 2) having an upper part 17a and a lower part 17b (FIG. 1), while an in particular manually operable (lower) housing part 18 is releasable fixed, particularly fitted or held onto the inner part 17, preferably by means of a retaining element 19. Preferably, the housing parts 16 and 18 form a housing of the nebulizer 1. In order to insert and/or replace the container 3 the housing can be opened and/or the housing part 18 can be detached from the nebulizer 1 or its housing.

The actuation member, preferably the housing part 18, can be actuated, here rotated relative to the upper housing part 16, carrying with it of driving the inner part 17. As a result the drive spring 7 is tensioned in the axial direction by means of a gear or transmission (not shown) formed between the inner part 17, in particular its upper part 17a, and the holder 6 and acting on the holder 6. During tensioning the container 3 is moved axially downwards until the container 3 assumes an end position as shown in FIG. 2. In this activated or tensioned state the drive spring 7 is under tension and can be caught or held by the blocking member 8. During the nebulizing process the container 3 is moved back into its original position (non-tensioned position or state shown in FIG. 1) by the drive spring 7. Thus the container 3 executes a lifting or stroke or linear movement or a back and forth movement during the tensioning process or conveying of fluid 2 and/or during the pressure generation or nebulization (process).

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 comprises preferably a container counter 23, which counts the number of containers 3 that have been or still can be used with or inserted into the nebulizer 1, preferably by detecting tensioning of the nebulizer 1 or its drive spring 7 or rotation of the inner part 17 relative to the upper part 16 of the housing. Preferably, the container counter 23 or a lock (preferably formed by a locking element or spring and actuated by the container counter 23) locks any (further) actuation or use of the nebulizer 1, e.g. blocks further rotation of the housing part 18/inner part 17 and, thus, tensioning of the nebulizer 1 or its drive spring 7, when a certain number of total actuations or operations or discharged doses has been reached or exceeded and/or when a predetermined number (e.g. four) of containers 3 have been inserted or used.

A preferred construction and mode of the inhaler or nebulizer 1 will now be described in more detail with reference to FIGS. 3 to 5, but emphasizing only essential differences from the nebulizer 1 according to FIGS. 1 and 2. The remarks relating to FIGS. 1 and 2 thus apply preferably accordingly or in a similar manner, while any desired combinations of features of the nebulizer 1 according to FIGS. 1 and 2 and the nebulizer 1 described below are possible.

FIG. 3 shows the nebulizer 1 in a delivery state with preferably pre-installed container 3 which is still closed. In this state, the housing of the nebulizer 1 is not completely closed, in particular the housing part 18 is not completely pushed on the inner part 17. FIGS. 4 and 5 show the nebulizer 1 in an activated and/or tensioned state with the housing completely closed and with the container 3 opened. In FIG. 4, the nebulizer 1 or drive spring 7 is tensioned, i.e. the container 3 is in its lower position. FIG. 5 shows the nebulizer 1 in a non-tensioned state, e.g. after the delivery or discharge of one dose of the fluid 2; the container 3 is in its upper position.

The container 3 comprises a fluid outlet 24 for outputting the fluid 2 to be dispensed. In particular, the fluid outlet 24 allows a fluidic connection between the container 3 or its bag 4 on one hand and the nebulizer 1, its pressure generator 5 or the conveying element on the other hand.

The fluid outlet 24 has an inner closure 25 that is preferably formed by a septum, a membrane, a plastic seal or the like and/or is provided inside the container 3. Optionally, a second or outer closure 26 can be provided such that successive opening is possible by means of one common element, in particular the conveying element or conveying tube 9 or the like, and/or by piercing.

Preferably, the first or inner closure 25 is formed or supported by a closure part 27 extending from the outlet or head end of the container 3 into the container 3 or bag 4. The second or outer closure 26 is preferably located adjacent to the head or axial end of the container 3 and/or held or connected to a flange 28, which can be formed by the closure part 27 or any other suitable part. However, other constructional solutions are possible.

In the delivery state according to FIG. 3, the container 3 has been pre-installed, i.e. inserted into the nebulizer 1. However, the container 3 or its fluid outlet 24 is not yet opened. In particular, the second closure 26 is already opened, but not the first closure 25. This is achieved in particular in that the housing of the nebulizer 1 is closed only partly, i.e. not completely, in the delivery state.

In particular, the container 3 is attached to or held by or secured in the housing part 18, in particular by a transportation lock 29, which is preferably arranged within or at the housing part 18. The transportation lock 29 holds the container 3 preferably temporarily, in particular before attaching the housing part 18 to the nebulizer 1 and/or in the delivery state. In particular, the transportation lock 29 holds the container 3 fixed during the fluidic connection of container 3 and/or during the mechanic connection of container 3, here with holder 6. Preferably, the transportation lock 29 holds the container 3 fixed during opening, in particular piercing, the container 3.

In the delivery state, in which the nebulizer 1 can be shipped or delivered to the user or is still packed, the nebulizer 1 or the housing part 18 is preferably secured, in particular by means of a securing member 30, e.g. a banderole, such that the container 3 and/or housing part 18 are held sufficiently spaced from the nebulizer 1 or upper housing part 16 and/or prevented from being completely inserted or pushed on the conveying element or tube 9, the housing or inner housing part 17 or the like and/or such that (complete) opening of the container 3, namely of the first closure 25, is prevented.

Once the security member 30 has been removed a user (not shown) can push the housing part 18 fully on in the axial direction and thereby open the container 3, i.e. first closure 25, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9).

FIG. 4 shows the nebulizer 1 or container 3 in the activated state, the container 3, i.e. first closure 25, is open, i.e. the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time. During this tensioning process the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a venting hole 34 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, non-tensioned state, i.e. after atomization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e. the nebulizer 1 remains activated.

To prevent unwanted opening of the container 3, particularly of the first closure 25, in the delivery state of the nebulizer 1, and/or to prevent (axial) movement of the container 3 relative to the associated housing part 18 before complete closing of the nebulizer 1, preferably the transportation lock 29 is provided. By frictional, forcible or interlocking engagement, for example, the transportation lock 29 prevents the container 3 from undesirably moving axially.

Preferably, the opening of the transportation lock 29 occurs automatically when closing the nebulizer 1 or its housing completely, i.e. when snapping or pushing on the housing part 18 completely towards the upper housing part 16. During this (preferably linear, axial or telescopic) closing movement, the transportation lock 29 is opened and the container 3 released (preferably not totally) in axial direction preferably only in a last part of the closing movement and/or just little before the final completely closed position is reached or just when the final completely closed position is reached.

The closing movement of the nebulizer 1 opens the transportation lock 29 preferably automatically. In particular, the transportation lock 29 is opened by the direct or indirect interaction with or actuation by the housing of the nebulizer 1, the inner part 17 or its lower part 17*b*, a holding ring 43 bearing the spring 7 or the like. Preferably, the container 3 and/or first closure 25 are opened as well as the transportation lock 29 by means of a common actuation, here the closing movement of the nebulizer 1 or its housing or lower part 18.

FIGS. 4 and 5 show the transportation lock 29 in the open position, i.e. wherein the container 3 is free to move axially.

In the following, the inhaler or nebulizer 1 according to the present invention will be described in detail with reference to FIGS. 6 to 13, wherein only essential differences will be emphasized so that the previous remarks and explications relating to the nebulizers 1 according to FIGS. 1 to 5 apply preferably in a corresponding or similar manner.

FIG. 6 shows in a very schematic, partially sectional view the nebulizer 1 according to a preferred embodiment of the present invention. The nebulizer 1 is shown in a transitional state from the delivery state to the activated state with not completely closed housing or housing part 18. The housing part 18 has already been pushed on the inner part 17 more than initially provided in the delivery state such as shown in FIG. 3. Therefore, the container 3 has already been opened in the state shown in FIG. 6. Further, the securing member 30, which preferably secures the housing part 18 in the delivery state against pushing on the inner part 17, has already been released or opened or removed in the state shown in FIG. 6. However, it is not necessary that the container 3 and the associated, preferably inseparable housing part 18 are pre-installed or pre-mounted to the nebulizer 1 or inner part 17 in the delivery state. Instead, the housing part 18 and the container 3 can be attached to the nebulizer 1 when using the nebulizer 1 for the first time, i.e. when closing the nebulizer 1.

The nebulizer 1 or its housing comprises a securing means 35 for holding the container 3 such that the container 3 is moveable back and forth for the conveying of the fluid 2, pressure generation and/or nebulization, but is inseparable from the housing or housing part 18, and/or such that the container 3 is unmoveably held in the delivery state of the nebulizer 1 and/or before closing the nebulizer 1. Preferably, the securing means 35 forms the transportation lock 29.

The securing means 35 is located or arranged preferably at or in the housing part 18 as shown in FIG. 6.

FIG. 7 shows in a perspective view a preferred embodiment of the securing means 35. FIG. 8 shows the securing means 35 connected with the container 3.

Preferably, the securing means 35 comprises or consists of a metal and/or stamping part and/or consists of a single, unitary part as shown in FIG. 7.

Preferably, the securing means 35 is made of steel, in particular spring steel.

Preferably, the securing means 35 is produced from sheet material by cutting, stamping or the like and/or by bending.

Preferably, the securing means 35 or the part forms a cage, in particular, encompasses the container 3 or an end portion thereof.

Preferably, the securing means 35 comprises holding elements 36 and/or supporting elements 37. The elements 36 and 37 are preferably designed like arms, fingers leaves or the like. In particular, the elements 36, 37 are alternately distributed over a circumference of the container 3 and/or extend at least essentially axially or in the direction of the back and forth movement of the container 3.

Preferably, the elements 36 and 37 are held by or connected with a base 38 of the securing means 35.

Preferably, the securing means 35 or base 38 comprises or holds the piercing element 22 for piercing the container 3, i.e. opening the container base 21 or its venting hole 34 in the activated and tensioned state, i.e. when the container 3 reaches its lower end position. In the shown embodiment, the piercing element 22 is formed by a respective bending of a spring portion 39 of the securing means 35 or its base 38. The spring portion 39 can support or facilitate the (complete or final) connection of the container 3 to holder 6.

The securing means 35 or base 38 comprises preferably at least one or multiple fixing portions 40 for fixing the securing means 35 at or in the nebulizer 1 or housing or housing part 18. In particular, the fixing portions 40 may fix the securing means 35 when the securing means 35 is pressed into the housing part 18 by cooperating with the side wall of the housing part 18. However, it is also possible to overmold the securing means 35, its base 38, the fixing portions 40 or the like. Moreover, the securing means 35 could be connected with the housing part 18 or the like in any other suitable manner.

Preferably, the securing means 35 does not only prevent the separation of the container 3 from the nebulizer 1, its housing or housing part 18, but also forms the transportation lock 29 for holding the container 3 unmovable in the housing in the delivery state of the nebulizer 1. FIGS. 6 and 8 shows this state or situation when the container 3 is held (axially) unmovable by the securing means 35, i.e. when the transportation lock 29 is closed. In this situation, the container 3 or its preferably radially protruding end or edge 41 of the container 3 or base 21 is held between the holding element(s) 36 and supporting element(s) 37, in particular between respectively formed or bent ends of the elements 36 and 37.

In the shown embodiment, the container end or edge 41 is caught between end portions 36*a* and 37*a* of the elements 36 and 37. The holding elements 36 grip or extend over the edge 41 and the supporting elements 37 or its end portions 37*a* grip or extend under the edge 41 or container base 21 so that the edge 41 and container 3 are securely held preventing any axial movement of the container 3 relative to the securing means 35 and relative to the associated housing part 18 in this state, i.e. with locked securing means 35/transportation lock 29.

When the securing means 35 or transportation lock 29 is closed, the supporting elements 37 or its end portions 37*a* hold or support the container 3 for opening by inserting the conveying element or tube 9, preferably wherein a press fit is formed between the conveying element or tube 9 and the container 3 or closure part 27, and/or for (completely) connecting the container (head) to the holder 6. With other words, the transportation lock 29 or securing means 35 or supporting elements 37 or end portions 37*a* form preferably a counter-bearing for the container 3 during closing of the nebulizer 1.

The holding element 36 and the supporting elements 37 are distributed alternatingly around the container 3 or edge 41.

Preferably, the end portions 36*a* of the holding elements 36 end in a first radial plane and the end portions 37*a* of the supporting elements 37 end in another, second radial plane, wherein the two planes are axially offset to hold the edge 41 in between and/or wherein the second plane is located axially between the first plane and the lower end position of the container 3 or the lower end of the housing part 18 or the piercing element 22. Additionally or alternatively, the end portions 36*a* end on another radius (outer radius) than the end portions 37*a* and/or are axially spaced therefrom.

The end portions 36*a* and/or 37*a* are preferably form like claws or the like and/or extend preferably radially inwardly.

Preferably, the elements 36 and/or 37 can flex with its free ends radially outwardly.

For example, the ends of the end portions 36*a* may be inclined such that the container 3 may be inserted into or connected with the securing means 35 by a respective axial force so that the holding elements 36 flex outwardly to allow passing of edge 41. However, the holding elements 36 can be flexed outwardly also by a suitable tool (not shown) or the like when the container 3 is inserted, in particular with its edge 41, into the securing means 35.

Preferably, the holding elements 36 prevent separation of the container 3 from the securing means 35 and, thus, from the associated housing part 18 or the like.

The supporting elements 37 or its end portions 37*a* can be flexed radially outwardly in order to open the axial holding or transportation lock 29 (this will be explained in detail with reference to FIG. 9 in the following). Then, the container 3 can axially move, in particular back and forth and/or with its edge 41 between the first plane and the piercing element 22 in the present embodiment.

In the present embodiment, the supporting elements 37 comprise actuation portions 37*b* (preferably formed at the free ends and/or between adjacent end portions 37*a*). Preferably, the actuation portions 37*b* form axial extensions which may be radially offset. The actuation portion 37*b* cooperate with an associated control member 42 or multiple control members 42 of the nebulizer 1 such that the locking elements 37 are flexed radially outwardly when (completely) closing the housing to open the transportation lock 29 (here primarily formed by the locking elements 37 or its end portions 37*a*).

FIG. 6 shows schematically the control member 42 axially spaced from the associated actuation portion 37*b* as the housing has not yet been closed (completely).

FIG. 9 shows a lower part of the completely closed nebulizer 1 with opened transportation lock 29, i.e. with radially outwardly flexed supporting elements 37. FIG. 9 shows that the control member 42 has an inclined guiding surface or the like to convert the axial closing movement into the radial opening movement of the actuation portion 37*b* and, thus, of the associated supporting element 37 to open the transportation lock 29, in particular when the housing has been completely closed or when the housing part 18 has been pushed completely on the nebulizer 1.

The control member 42 is preferably formed as an axial protrusion. It can be formed by or at a ring 43 or any other bearing means of the nebulizer 1 for counter-bearing the drive spring 7 in the inner part 17 or by or at any other suitable component if the nebulizer such as the inner part 17.

The control member 42 may be formed like an axial protruding ring or shoulder or ridge which extends along the ring 43.

The control member 42 may additionally secure the holding elements 36 against axial opening when the housing is completely closed as schematically shown in FIG. 9. In this case, the control member 42 contacts the holding element(s) 36 or its end portions 36*a* peripherally on the outer side to prevent any outward flexing. Then, the securing means 35 or its holding elements 36 are secured against opening so that the container 3 is securely held within the securing means 35 or the cage formed by the securing means 35 or holding elements 36.

FIG. 9 shows the container 3 in its lower position when the piercing element 22 can pierce the venting hole 34 or an associated seal attached to the container base 21.

In the present embodiment, the securing means 35 has multiple functions. It holds the container 3 (in the activated state/with completely closed housing) such that it can move back and forth, in particular during conveying of the fluid 2, during pressure generation and/or during nebulization, wherein the container 3 is inseparable from the housing or the housing part 18. Further, the securing means 35 forms the transportation lock 29 and/or holds the container 3 unmovable in the delivery state of the nebulizer 1 and/or for opening the container 3 and/or for connecting the container 3 to the holder 6 and/or conveying tube 9. Additionally or alternatively, the securing means 35 comprises an opening means, here the piercing element 22, for opening the venting hole 34 of the container 3.

Preferably, the securing means 35 forms a cage which cannot be separated from the container 3 after connecting it with the container 3.

The transportation lock 29 and the supporting elements 37 are kept opened during the normal use of the nebulizer 1, in particular as long as the housing is (completely) closed. When the housing is opened, i.e. the housing part 18 is detached, the control member 42 may disengage from the actuation portions 37*b* so that the supporting elements 37 can close or flex inwardly again. Then, the supporting elements 37 may grip with its end portions 37*a* over the edge 41 of the container 3 such that an additional lock is formed which prevents that the container 3 can be separated from the securing means 35/housing part 18.

The securing means 35 prevents separation of the container 3 from the housing part 18. Therefore, the container 3 can be replaced or exchanged only together with the housing part 18 if the housing part 18 can be detached from the nebulizer 1 or inner part 17 at all. If the nebulizer 1 is in a state that it cannot be opened, i.e. is blocked against opening, the container 3 cannot be replaced.

FIG. 10 shows in a schematic view the nebulizer 1, wherein an outer part or shell of the (lower) housing part 18 and the securing means 35 are not shown. Instead, an inner member 44 of the housing part 18 is shown. The inner member 44 is connected, attached or pushed on the nebulizer 1 or, in particular, its inner part 17.

Preferably, the inner member 44 is rigidly and/or inseparably connected with the housing part 18. In particular, the inner member 44 is arranged within or received by the housing part 18. With other words, the housing part 18 encompasses its inner part 44 normally.

The nebulizer 1 comprises an operation counter 45 for counting uses or operations of the nebulizer 1 with the associated or current container 3. The operation counter 45 is arranged at or within the housing part 18, e.g. between the housing part 18 and its inner member 44.

Preferably, the operation counter 45 is inseparable from the housing part 18 for replacement together with the container 3 and the housing part 18.

The operation counter 45 comprises preferably a first lead screw 46 and an associated, first rider 47. Preferably, both the first lead screw 46 and the first rider 47 are supported by the housing part 18 directly or indirectly, e.g. between the housing part 18 and its inner member 44 and/or by any other suitable bearing means attached thereto.

The operation counter 45 or first lead screw 46 is preferably driven by the rotation of the housing part 18 and/or inner member 17 relative to the nebulizer 1 or its upper housing part 16, in particular during conveying of fluid 2 into the pressure generator 5 or into the pressure chamber 11 and/or during tensioning of the drive spring 7. In the present embodiment, the first lead screw 46 extends parallel to this rotational axis.

Preferably, the first lead screw 46 comprises a gear 48 at its upper end extending into the nebulizer 1 or upper housing part 16 and, in particular, meshing with an inner toothing 49. However, other constructional solutions are possible.

The first rider 47 meshes with the first lead screw 46 and is linearly and/or axially moveable depending on the rotation of the first lead screw 46.

Preferably, the operation counter 45 locks the nebulizer 1 against further use, in particular against conveying of fluid 2 into the pressure generator 5 or pressure chamber 11, against tensioning of the drive spring 7, against rotation of the housing part 18, against pressure generation and/or nebulization, in a first locked state when a predetermined number of uses has been reached or exceeded with the current or associated container 3. For this purpose, the nebulizer 1 or operation counter 45 comprises preferably a first lock or locking element 50, in particular a spring. In particular, the first locking element 50 is arranged at and/or guided by and/or attached to and/or inseparable from the housing part 18 and/or its inner member 44.

In the present embodiment, the first locking element 50 can be shifted or moved preferably axially towards or into the nebulizer 1 or its upper housing part 16 and/or between the inner part 17 and upper housing part 16 and/or such that it expands in axial direction, preferably such that the locking element 50 blocks in this locking position or upwardly moved or shifted position (shown in dashed line in FIG. 10) any further rotation of the inner part 17 and/or lower housing part 18, in particular relative to upper housing part 16. This can be achieved, in particular in that the locking element 50 or spring is axially biased and/or can engage into at least one respective recess or the like and/or can catch a stop or the like in the locking position so that the desired blocking effect is achieved in the locking position of the first locking element 50.

For example, the spring or locking element 50 can be formed by a bent or biased metal sheet part or the like, which can expand or open when moved upwards or into the locking position, but can not be moved back into the lower position as it blocks itself, i.e. by abutment at the inner part 17, inner member 44 and/or housing part 18.

However, other constructional solutions are possible as well.

In the present embodiment, the first locking element 50 is preferably moved into the locking position or is moved sufficiently to overcome a respective catch, resistance or the like for moving into the locking position by the first rider 47, in particular by a respective abutting portion 51 of the first rider 47 when the first rider 47 reaches an upper position (indicated in dashed line in FIG. 10).

In the locking position, the lock or locking element 50 blocks or locks the nebulizer 1 against further use. This state is called first locked state. Preferably, this first locked state is reversible or can be reset by replacing or exchanging the housing part 18 together with the container 3 and the operation counter 45. In particular, the locking element 50 will be withdrawn and detached together with the housing part 18 by the replacement of the housing part 18.

Preferably, the nebulizer 1 is blocked against opening or detachment of the housing part 18 until a predetermined number of uses has been reached or exceeded with the current or associated container 3.

In particular, the nebulizer 1 comprises a first opening lock 52 which blocks opening of the nebulizer 1 or detachment of the housing part 18 and, thus, blocks container replacement. This first opening lock 52 is preferably opened by the operation counter 45 or its first rider 47 when the predetermined number of uses has been reached or exceeded with the associated or current container 3.

In the present embodiment, the first opening lock 52 comprises a first locking portion 53 which is preferably flexible and/or arm-like. In particular, the first locking portion 53 is formed by or attached to the housing part 18 and/or its inner member 44. However, other constructional solutions are possible as well.

Preferably, the first locking portion 53 blocks automatically the nebulizer 1 or housing part 18 against opening or detachment when closing the nebulizer 1, in particular when pushing the housing part 18 onto the nebulizer 1 or its inner part 17. Preferably, the first locking portion 53 flexes over a protrusion or stop 54 formed at or attached to the inner part 17 and/or extending preferably radially.

The first opening lock 52 or first locking portion 53 is opened or unlocked by the counter device 45 or the first rider 47 when the predetermined number of uses has been reached or exceeded with the associated or current container 3. For this purpose, the first rider 47 comprises preferably an actuation portion 55 which can actuate or flex the first opening lock 52 or first locking portion 53. In particular, the actuation portion 55 comprises an inclined surface cooperating or interfering with the first opening lock 52, in particular with a preferably inclined control portion 56 of the locking portion 53 or the like, such that the first rider 47 or its actuation portion 55 can flex the first locking portion 53 (preferably in circumferential direction as indicated in FIG. 10 in dashed line) out of engagement or interference with stop 54 so that the first opening lock 52 is opened and the housing part 18 can be detached from the nebulizer 1 for container replacement.

The first opening lock 52 or its first locking portion 53 is shown in the unlocked or flexed position in dashed line as in dashed line as in its lower position, but not in its upper position wherein it opens or flexes the first locking portion 53 and actuates the first locking element 50.

FIG. 11 shows the nebulizer 1 in a view similar to FIG. 10, but from the opposite side. In particular, the housing part 18 and the securing means 35 are not shown in FIG. 11, but the inner member 44 of the housing part 18 is shown attached to the inner part 17. In particular, FIG. 11 shows a preferred realization of the container counter 23.

Preferably, the container counter 23 counts the number of containers 3, which have been used or still can be used, and/or the total or overall number of uses or operations of the nebulizer 1 which have already performed or which still can be performed (with all containers 3). Thus, the container counter 23 can restrict the total number of uses or operations that are possible with the nebulizer 1.

The container counter 23 comprises preferably a second lead screw 57 and an associated, second rider 58 in the present embodiment.

The container counter 23 is preferably attached to or inseparable from the nebulizer 1 or inner part 17. In particular, the second lead screw 57 and second rider 58 are supported by or beared at the inner part 17.

Preferably, the container counter 23 or the second lead screw 57 is driven by the rotation of the housing part 18 and/or inner part 17, in particular relative to the nebulizer 1 or upper housing part 16, and/or during conveying of fluid 2 into the pressure generator 5 or pressure chamber 11 and/or during tensioning of the drive spring 7.

In the present embodiment, the second lead screw 57 comprises at its upper end a gear 59 meshing with the inner toothing 49. However, other constructional solutions are possible.

The nebulizer 1 or container counter 23 comprises preferably a second lock or locking element 60, as schematically shown in FIG. 1. Preferably, the second locking element 60 is formed by a preferably pre-biased spring or the like. In the present embodiment, the second locking element 60 can be actuated or moved by the container counter 23 or its second rider 58, in particular by an abutting or pushing portion 61 schematically shown in FIG. 1. When the second rider 58 moves from its lower position shown in FIG. 11 in an upper position (shown in dashed line), the portion 61 can move or push the second locking element 60 into a locking position where the locking element 60 can expand and/or lock the nebulizer 1 against further use, in particular by locking or blocking the inner part 17 against rotation relative to the upper housing part 16. This locked state is called second locked state or final locked state.

The nebulizer 1 is locked against further use in the second locked state when a predetermined number of total uses has been reached or exceeded with all containers 3 and/or when a predetermined number of containers 3 has been inserted or used with the nebulizer 1.

The second locked state is preferably not reversible, i.e. is final.

The nebulizer 1 or container counter 23 comprises preferably a second opening lock 62 which blocks opening of the nebulizer 1 or detachment of the housing part 18 and, thus, blocks container replacement in the second locked state. In particular, the second opening lock 62 is closed when or before a predetermined number of used or inserted containers 3 has been reached or exceeded and/or before reaching the second locked state and/or when a predetermined number of uses of the nebulizer 1 has been reached or exceeded. Preferably, the second opening lock 62 is associated to the container counter 23 for blocking opening of the nebulizer 1.

In the present embodiment, the second opening lock 62 comprises preferably a second locking portion 63. The second locking portion 63 is preferably flexible and/or arm-like or hook-like.

The second locking portion 63 is preferably formed by or attached to the housing part 18 its inner member 44. However, other constructional solutions are possible as well.

Preferably, the second locking portion 63 can lock or interfere or abut against a stop 64 in the locking or flexed position shown in dashed line in FIG. 11. The stop 64 is preferably formed at or by the inner part 17 and/or by a radial protrusion or the like. Thus, detachment of the housing 17 is blocked in the locking position by the closed second opening lock 62 in the second locked state.

Preferably, the container counter 23 or second rider 58 operates or actuates the second opening lock 62, in particular flexes or moves the second locking portion 63 into the locking position. For this purpose, the second rider 58 comprises preferably an actuation portion 65, in particular with an inclined surface, which interferes or cooperates with the second locking portion 63, in particular with a preferably inclined control portion 66 of the second locking portion 63, such that the second opening lock 62 is closed and/or the second locking portion 63 is flexed or moved into the locking position (shown in dashed line) when the second rider 58 approaches or reaches its upper position shown in dashed line in FIG. 11.

The second locking portion 63 is preferably formed by or attached to the housing part 18 its inner member 44. However, other constructional solutions are possible as well.

It has to be noted that the second locking element 60 is only optional and that the second opening lock 62 can be sufficient in combination with first locking element 50 or the first opening lock 52 to lock the nebulizer 1 in the second locked state against any further use. However, the second locking element 60 provides or allows preferably the strongest locking of the nebulizer 1.

FIG. 12 shows an alternative embodiment in a view similar to FIG. 10, wherein the construction of the first locking element 50 is modified or changed. In particular, the first locking element 50 can be formed by the first rider 47 itself or its abutting portion 51. In this case, the rider 57 or a portion thereof extends preferably upwards and/or in axial direction such that, in the upper position (locking position) of the first rider 47 shown in FIG. 12, the desired rotational locking of the nebulizer 1 is achieved.

In order to ensure an abrupt rotational lock or a prompt and complete entering of the locking portion or first locked state, the first rider 47 can be biased upwardly by a spring 68, e.g. arranged around the first lead screw 46. Preferably, the threading 67 of the first lead screw 46 is preferably shortened such that the meshing of the first rider 47 with the first lead screw 46 ends before the first rider 47 reaches its upper position and is biased by the force of the spring 68 into its final upper position. However, other constructional solutions are possible as well.

If desired, the alternative embodiment mentioned above can be realized additionally or alternatively at the container counter 23.

As already explained, the operation counter 45 is preferably associated or connected to the housing part 18. The container counter 23 is preferably associated or connected to the nebulizer 1 or inner part 17. With other words, the two counters 23 and 45 are preferably separated positively when detaching or opening the nebulizer 1 or housing part 18, in particular when replacing the housing part 18 together with the respective container 3 and the operation counter 45.

FIG. 13 shows in a schematic section the nebulizer 1 with separated housing part 18 and container 3, preferably before connecting the housing part 18 and container 3 to the nebulizer 1. In particular, the nebulizer 1 can be delivered also in this state, i.e. with separated housing part 18 and separated container 3.

Preferably, the nebulizer 1 is delivered with multiple containers 3 each inseparably connected to a respective housing part 18 and operation counter 45.

Preferably, the operation counter 45 or first lead screw 46 on one hand and the container counter 23 or second lead screw 57 are located on opposite sides or in positions offset by exactly or about 180° at the inner part 17 or housing part 18, respectively.

FIG. 13 shows how the inner member 44 is held or received in the housing part 18, in particular by a respective snap fit, press fit or the like.

Preferably, the first opening lock 52 is associated to and/or operated by the operation counter 45. Preferably, the second opening lock 62 is associated to and/or operated by the container counter 23.

Preferably, the first locked state is reversible or can be reset, in particular by replacing the housing part 18 and/or operation counter 45 and/or first locking element 50.

Preferably, the second locked state is irreversible and/or forms a final locked state of the nebulizer 1.

Preferably, the operation counter 45 is located in an area where the retaining element 19 was located initially.

The operation counter 45 and/or first opening locked 52 can replace the retaining element 19. In particular, the retaining element 19 can be omitted or can be located differently and/or realized by another constructional solution (not shown).

The operation counter 45 and/or container counter 23 may comprise associated markings, scales or the like, in particular to show or indicate the current count, such as the number of operations already performed or still possible with the current container 3, the total number of operations already performed or still possible with all containers 3 and/or the number of containers 3 already inserted or used or that can still be inserted or used. Alternatively or additionally, any necessary or performed container change can be shown or indicated.

Preferably, the respective count is indicated or shown by the respective rider 47 or 58, in particular by the position of the respective rider 47 or 58.

Preferably, the nebulizer 1 or housing part 18 is at least partially transparent and/or provided with a window or the like so that the respective count or rider position is visible for the user.

It is pointed out that the container counter 23 can be omitted if desired. Alternatively or additionally, the housing parts 18, that can be connected to the same nebulizer 1, may be different such that, in particular, the last housing part 18 is designed such and/or cooperates with the nebulizer 1 such that the opening lock 52 does not open any more, e.g. by omitting the actuation portion 55.

Additionally or alternatively, the housing parts 18 can be marked differently at least the one which is to be used last. Thus, a user will use the different housing part 18 in a predetermined or desired sequence and/or at least one designated housing part 18 last. For this purpose or generally, the housing parts 18 may be numbered or provided with colors and/or any other markings.

It is noted that the nebulizer 1 shown in FIGS. 10 to 13 comprises a cover 69 covering the mouthpiece 13. This cover 69 is opened before using the nebulizer 1, in particular before inhaling.

As already mentioned, individual features, aspects and/or principles of the embodiments described may also be combined with one another as desired and may be used particularly in the nebulizer according to FIGS. 1 and 5 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation or an ethanolic pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/115200 A1, preferably pages 25 to 40, which is incorporated herewith by reference. In particular, these may be aqueous or non-aqueous solutions, mixtures, formulations containing ethanol or free from solvent, or the like.

LIST OF REFERENCE NUMERALS 1 nebulizer
2 fluid
3 container
4 bag
5 pressure generator
6 holder
7 drive spring
8 blocking element
9 conveying tube
10 non-return valve
11 pressure chamber
12 nozzle
13 mouthpiece
14 aerosol
15 air supply opening
16 upper housing part
17 inner part
17a upper part of the inner part
17b lower part of the inner part
18 housing part (lower part)
19 retaining element
20 spring
21 container base
22 piercing element
23 container counter
24 fluid outlet
25 first closure
26 second closure
27 closure part
28 flange
29 transportation lock
30 securing member
31 (not used)
32 (not used)
33 (not used)
34 venting hole
35 securing means
36 holding element
36a end portion
37 supporting element
37a end portion
37b actuation portion
38 base
39 spring portion
40 fixing portion
41 edge
42 control member
43 ring
44 inner member 45 operation counter
46 first lead screw
47 first rider
48 gear
49 inner toothing
50 first locking element
51 abutting portion
52 first opening lock
53 first locking portion
54 stop
55 actuation portion
56 control portion
57 second lead screw
58 second rider
59 gear
60 second locking element
61 pushing portion
62 second opening lock
63 second locking portion
64 stop
65 actuation portion
66 control portion
67 threading
68 spring
69 cover

The invention claimed is:

1. A nebulizer (1) which is an inhaler for a fluid (2), comprising:
   a replaceable container (3) containing the fluid (2),
   a housing part (18), which is detachable from the nebulizer (1) for replacing the container (3) and which is inseparable from the container (3),
   an operation counter (45) for counting each use of the nebulizer (1) drawing the fluid from the replaceable container (3), the operation counter (45) including a first lead screw (46) and an associated, first rider (47), where the use of the nebulizer causes movement of the first rider (47) and the first lead screw (46) to register such use, wherein the operation counter (45), including the first lead screw (46) and the first rider (47), is disposed entirely within, and are inseparable from, the housing part (18), such that the operation counter (45) is replaced together with the container (3) when the housing part (18) is removed from the nebulizer (1) and replaced, and
   a use opening lock (52) that blocks opening of the nebulizer (1) or detachment of the housing part (18) and, thus, blocks container replacement, based on uses of the nebulizer (1) with the replaceable container (3), wherein the use opening lock (52) is opened by the operation counter (45) or first rider (47) when a predetermined number of uses has been reached or exceeded with the replaceable container (3).

2. The nebulizer according to claim 1, wherein the first lead screw (46) is driven by relative rotation of the housing part (18) and/or during conveying of fluid (2) into a pressure generator (5) or pressure chamber (11) of the nebulizer (1) and/or during tensioning of a drive spring (7) of the nebulizer (1).

3. The nebulizer according to claim 1, wherein the operation counter (45) locks the nebulizer (1) against further use conveying of fluid (2) into a pressure generator (5) of the nebulizer (1), tensioning of a drive spring (7) of the nebulizer (1), rotation of the housing part (18), pressure generation and/or nebulization, in a first locked state when a predetermined number of uses has been reached or exceeded with the current or associated container (3).

4. The nebulizer according to claim 3, wherein the housing part (18) guides a first locking element (50) which is a spring or a spring biased element, whereby for entering the first locked state the first locking element (50) is moved into a locking position by or together with the first rider (47) for entering the first locked state.

5. The nebulizer according to claim 3, wherein the first locked state is reset by replacing the housing part (18) together with the container (3) and operation counter (45).

6. The nebulizer according to claim 1, further comprising: a container opening lock (62) that blocks opening of the nebulizer (1) or detachment of the housing part (18) and, thus, blocks container replacement, based on a predetermined number of container replacements, wherein the container opening lock (62) is closed when the predetermined number of container replacements or, when a predetermined number of uses of the nebulizer (1) has been reached or exceeded.

7. The nebulizer according to claim 6, wherein the nebulizer (1) comprises a container counter (23) counting the number of containers (3) that have been used or inserted or still can be used or inserted.

8. The nebulizer according to claim 7, wherein the container counter (23) closes the container opening lock (62).

9. The nebulizer according to claim 7, wherein the container counter (23) actuates or comprises a second lead screw (57) and an associated, second rider (58).

10. The nebulizer according to claim 9, wherein the second rider (58) actuates or closes the container opening lock (62).

11. The nebulizer according to claim 1, wherein the container (3) is pre-assembled into the housing part (18).

12. The nebulizer according to claim 1, wherein the container (3) is moveable back and forth within the nebulizer (1) and/or relative to the housing part (18) of the nebulizer (1) during conveying of fluid (2), pressure generation and/or nebulization.

13. The nebulizer according to claim 1, wherein the nebulizer (1) comprises a securing mechanism (35) operating to hold the container (3) inseparably in the housing part (18), wherein the container (3) is moveable back and forth within the housing part during conveying of fluid (2), pressure generation and/or nebulization.

* * * * *